United States Patent
Wallace et al.

(10) Patent No.: US 6,936,042 B2
(45) Date of Patent: Aug. 30, 2005

(54) SURGICAL TOOLS FOR USE IN MINIMALLY INVASIVE TELESURGICAL APPLICATIONS

(75) Inventors: Daniel T. Wallace, Redwood City, CA (US); Christopher A. Julian, Los Gatos, CA (US); Tracey A. Morley, Sunnyvale, CA (US); David S. Baron, Cupertino, CA (US)

(73) Assignee: Intuitive Surgical, Sunnyvale, CA (US)

( * ) Notice: Subject to any disclaimer, the term of this patent is extended or adjusted under 35 U.S.C. 154(b) by 115 days.

(21) Appl. No.: 10/124,169

(22) Filed: Apr. 16, 2002

(65) Prior Publication Data

US 2002/0111621 A1 Aug. 15, 2002

Related U.S. Application Data

(62) Division of application No. 09/398,958, filed on Sep. 17, 1999, now Pat. No. 6,394,998.
(60) Provisional application No. 60/116,844, filed on Jan. 22, 1999.

(51) Int. Cl.[7] .............................................. A61B 17/00
(52) U.S. Cl. ........................................................ 606/1
(58) Field of Search .................... 606/1, 167, 205–209, 606/41

(56) References Cited

U.S. PATENT DOCUMENTS

| | | |
|---|---|---|
| 4,038,987 A | 8/1977 | Komiya |
| 4,149,278 A | 4/1979 | Wiker et al. |
| 4,367,998 A | 1/1983 | Causer |
| 4,511,305 A | 4/1985 | Kawai et al. |

(Continued)

FOREIGN PATENT DOCUMENTS

| | | |
|---|---|---|
| WO | WO 99/50721 A1 | 10/1999 |

OTHER PUBLICATIONS

Madhani et al., (1998). "The black falcon: A teleoperated surgical instrument for minimally invasive surgery" (submitted to IROS 1998) 9 pages total.

Moyer, T.H., (1992). Thesis entitled "The design of an integrated hand and wrist mechanism" for Master of Science in Mechanical Engineering at the Massachusetts Institute of Technology, pp. 1–106.

Neisius, B. et al., (1994). "Robotic manipulator for endoscopic handling of surgical effectors and cameras," Proceedings of the First International Symposium on Medical Robotics and Computer Assisted Surgery, vol. 2, Workshop (Part I & II)—Session VI, pp. 169–175.

Salisbury, J.K., (1982). "Kinematic and force analysis of articulated hands" Department of Computer Science, Stanford University, Report No. STAN–CS–89–921 Chapter 9, pp. 67–77.

(Continued)

*Primary Examiner*—Roy D. Gibson
*Assistant Examiner*—Pete Vrettakos
(74) *Attorney, Agent, or Firm*—Townsend & Townsend & Crew

(57) ABSTRACT

This invention provides surgical tools or instruments for use in minimally invasive telesurgical applications. The instruments typically include a base whereby the instrument is removably mountable on a robotically controlled articulated arm. An elongate shaft extends from the base. A working end of the shaft is disposed at an end of the shaft remote from the base. A wrist member is pivotally mounted on the working end. At least one end effector element mounting formation is pivotally mounted on an opposed end of the wrist member. A plurality of elongate elements, e.g., cables, extend from the end effector element mounting formation and the wrist member to cause selective angular displacement of the wrist member and end effector mounting formation in response to selective pulling of the elongate elements.

54 Claims, 20 Drawing Sheets

U.S. PATENT DOCUMENTS

| | | | |
|---|---|---|---|
| 4,744,363 A | | 5/1988 | Hasson |
| 4,751,925 A | | 6/1988 | Tontarra |
| 4,766,775 A | * | 8/1988 | Hodge ..................... 74/490.01 |
| 4,837,703 A | | 6/1989 | Kakazu et al. |
| 4,928,546 A | | 5/1990 | Walters |
| 5,176,702 A | * | 1/1993 | Bales et al. ................. 606/208 |
| 5,318,589 A | * | 6/1994 | Lichtman .................... 606/205 |
| 5,354,296 A | * | 10/1994 | Turkel ......................... 606/41 |
| 5,445,638 A | * | 8/1995 | Rydell et al. ................. 606/51 |
| 5,520,678 A | | 5/1996 | Heckele et al. |
| 5,631,973 A | | 5/1997 | Green |
| 5,649,956 A | | 7/1997 | Jensen et al. |
| 5,695,500 A | | 12/1997 | Taylor et al. |
| 5,716,354 A | * | 2/1998 | Hluchy ........................ 606/46 |
| 5,762,458 A | | 6/1998 | Wang et al. |
| 5,797,900 A | | 8/1998 | Madhani et al. |
| 5,808,665 A | | 9/1998 | Green |
| 5,849,022 A | * | 12/1998 | Sakashita et al. ........... 606/174 |
| 5,876,325 A | | 3/1999 | Mizuno et al. |
| 5,964,780 A | * | 10/1999 | Balazs ........................ 606/208 |
| 6,152,920 A | * | 11/2000 | Thompson et al. ........... 606/41 |
| 6,190,399 B1 | * | 2/2001 | Palmer et al. .............. 606/205 |
| 6,206,903 B1 | * | 3/2001 | Ramans ...................... 606/205 |
| 6,276,312 B1 | * | 8/2001 | Summan et al. ......... 123/41.54 |
| 6,334,860 B1 | * | 1/2002 | Dorn ........................... 606/48 |

OTHER PUBLICATIONS

Thring, M.W. (1993). "Robots and telechirs: Manipulators with memory, remote manipulators, machine limbs for the handicapped," Halsted, pp. 9–11, 122–131, 194–195, 235–257, 274–279.

"Task 2: Miniature end effector—A preliminary design" pp. 32–47.

* cited by examiner

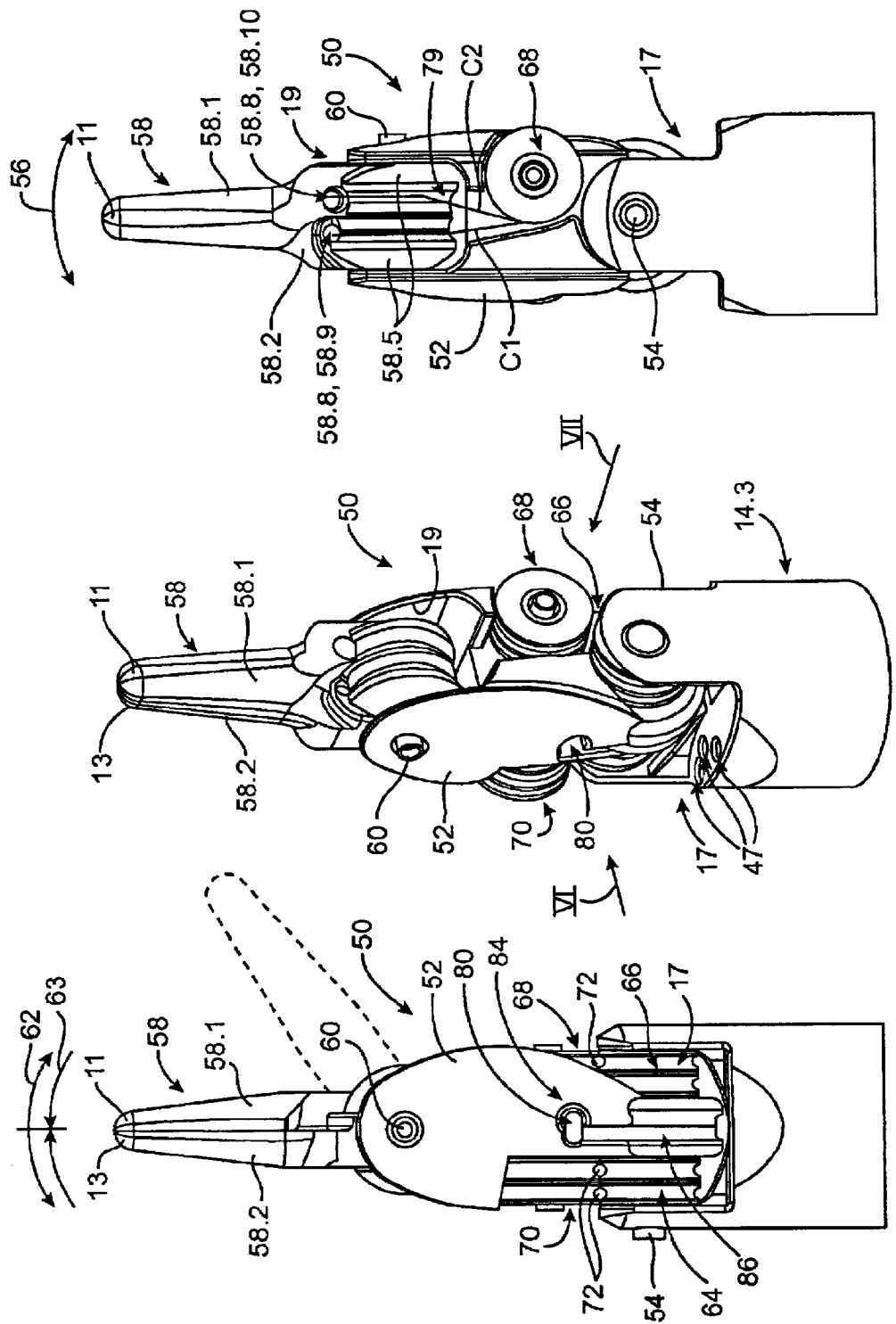

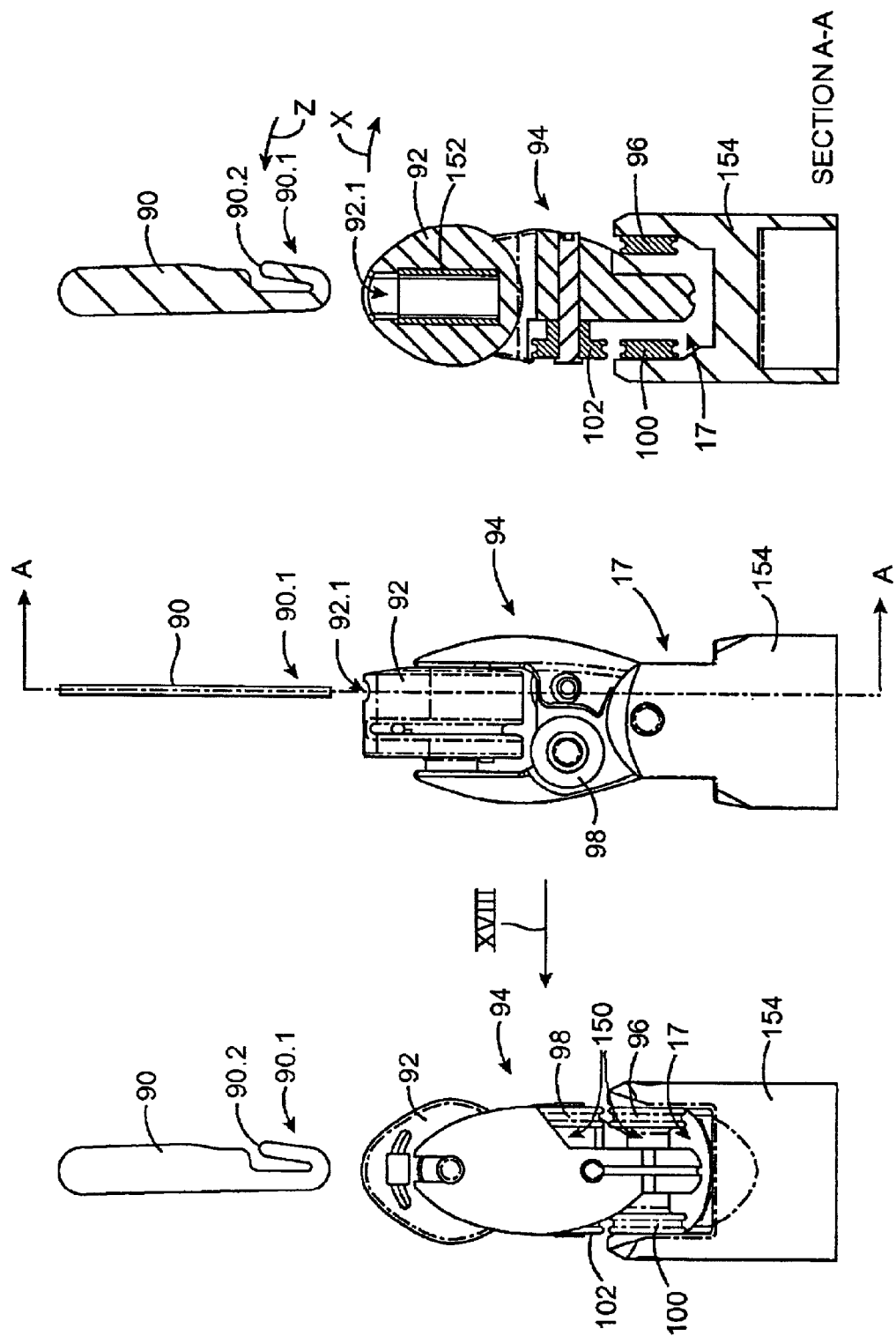

SURGICAL TOOLS FOR USE IN MINIMALLY INVASIVE TELESURGICAL APPLICATIONS

CROSS-REFERENCES TO RELATED APPLICATIONS

This is a divisional application of U.S. patent application Ser. No. 09/398,958, filed Sep. 17, 1999 now U.S. Pat. No. 6,394,998, which is a nonprovisional application of U.S. Patent Application Ser. No. 60/116,844, filed Jan. 22, 1999, the full disclosures of which are herein incorporated by reference.

BACKGROUND OF THE INVENTION

The present application is generally directed to medical devices, systems, and methods. In a particular embodiment, the invention provides telesurgical robotic tools, systems and methods.

Advances in minimally invasive surgical technology could dramatically increase the number of surgeries performed in a minimally invasive manner. Minimally invasive medical techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using minimally invasive surgical techniques. Thus, an increased adoption of minimally invasive techniques could save millions of hospital days, and millions of dollars annually in hospital residency costs alone. Patient recovery times, patient discomfort, surgical side effects, and time away from work may also be reduced with minimally invasive surgery.

The most common form of minimally invasive surgery may be endoscopy. Probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments. The laparoscopic surgical instruments generally include a laparoscope (for viewing the surgical field) and working tools. The working tools are similar to those used in conventional (open) surgery, except that the working end or end effector of each tool is separated from its handle by an extension tube. As used herein, the term "end effector" means the actual working part of the surgical instrument and can include clamps, graspers, scissors, staplers, and needle holders, for example. To perform surgical procedures, the surgeon passes these working tools or instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy and the like.

There are many disadvantages relating to current minimally invasive surgical (MIS) technology. For example, existing MIS instruments deny the surgeon the flexibility of tool placement found in open surgery. Most current laparoscopic tools have rigid shafts, so that it can be difficult to approach the worksite through the small incision. Additionally, the length and construction of many endoscopic instruments reduces the surgeon's ability to feel forces exerted by tissues and organs on the end effector of the associated tool. The lack of dexterity and sensitivity of endoscopic tools is a major impediment to the expansion of minimally invasive surgery.

Minimally invasive telesurgical robotic systems are being developed to increase a surgeon's dexterity when working within an internal surgical site, as well as to allow a surgeon to operate on a patient from a remote location. In a telesurgery system, the surgeon is often provided with an image of the surgical site at a computer workstation. While viewing a three-dimensional image of the surgical site on a suitable viewer or display, the surgeon performs the surgical procedures on the patient by manipulating master input or control devices of the workstation. The master controls the motion of a servomechanically operated surgical instrument. During the surgical procedure, the telesurgical system can provide mechanical actuation and control of a variety of surgical instruments or tools having end effectors such as, e.g., tissue graspers, needle drivers, or the like, that perform various functions for the surgeon, e.g., holding or driving a needle, grasping a blood vessel, or dissecting tissue, or the like, in response to manipulation of the master control devices.

At the working end of the robotic surgical instrument, a wrist-like mechanism may be provided between an end of the shaft and the end effector. The wrist-like mechanism enables the position or orientation of the end effector to be varied relative to the end of the shaft. The wrist-like mechanism may also be operatively connected to the master controls to enable the position or orientation of the end effectors to be varied by the surgeon manipulating the master controls.

It is to be appreciated that such a telesurgery system described above typically includes two robotic arms. Each arm typically carries a surgical instrument. Two master controls are typically provided, each of which is in operative communication with one of the arm and instrument systems, the master controls being arranged to be gripped in respectively the right and left hands of the surgeon.

It is an object of this invention to provide improved robotic surgical tools, devices, and methods. In one embodiment, the invention provides an improved wrist-like mechanism for use in a telesurgery system as described above. It is further an object of this invention to provide specific end effectors for use in conjunction with such a wrist-like mechanism.

SUMMARY OF THE INVENTION

In accordance with one aspect of the invention, a minimally invasive surgical instrument including an elongate shaft having a working end is provided. A wrist member having an end portion is pivotally mounted on the working end of the preferably substantially rigid shaft at its end portion by means of a pivotal connection. At least one end effector mounting formation is pivotally mounted by means of a pivotal connection on an opposed end portion of the wrist member. An elongate element length extends from each of two opposed positions on the end effector mounting formation and in a direction toward an opposed end of the shaft. The elongate element lengths are coupled to a driving member so as to cause angular displacement of the end effector mounting formation in one angular direction in response to the driving member causing one of the elongate element lengths to be pulled and to cause angular displacement of the end effector mounting formation in an opposed angular direction in response to the driving member causing the other elongate element length to be pulled. An elongate element length also extends from each of two opposed positions on the wrist member and in a direction toward the opposed end of the shaft, these elongate element lengths are coupled to another driving member so as to cause the wrist member to pivot about its pivotal connection in one angular direction in response to that driving member causing one of the elongate element lengths to be pulled and to cause the wrist member to pivot in an opposed angular direction in response to that driving member causing the other elongate element length to be pulled.

The minimally invasive surgical instrument may further include another end effector mounting formation and an elongate element length extending from each of two opposed positions on that end effector mounting formation and in a direction toward the opposed end of the shaft. These elongate element lengths may be coupled to yet a further driving member so as to cause the further end effector mounting formation to displace in one angular direction in response to the further driving member causing one of the elongate element lengths to be pulled and to displace in an opposed angular direction in response to the further driving member causing the other elongate element length to be pulled.

According to another aspect, a minimally invasive surgical instrument is provided which includes, a pair of end effector mounting formations each of which is arranged to carry an end effector element and to be displaceable so that the end effector elements move toward and away from each other in a plane of movement. The minimally invasive surgical instrument may further include an urging arrangement arranged to urge the end effector elements toward each other when they are moved apart beyond a predetermined amount. The urging arrangement may include a resilient urging member arranged to cooperate with the mounting formations so as to be resiliently deformed upon movement of the end effector elements beyond the predetermined amount thereby to urge the end effector elements toward each other. The resilient urging member may extend at an angle relative to the plane of movement.

According to a further aspect, a minimally invasive surgical instrument is provided which includes a pair of end effector mounting formations each of which is arranged to carry an end effector element and to be displaceable so that the end effector elements move toward and away from each other in a plane of movement. The minimally invasive surgical instrument may include an urging arrangement arranged to urge the end effector elements toward each other when they are moved apart beyond a predetermined amount. The urging arrangement may include at least one elongate resilient urging member one end of which is anchored on one of the mounting formations and an opposed free end of which intrudes into a space defined by the other mounting formation. The free end may be arranged to abut part of the other mounting formation defined at an end of the space when the end effector elements are moved apart by the predetermined amount, such that the resilient member is resiliently deformed by that part of the other mounting formation in response to the end effector elements being urged apart beyond the predetermined amount, thereby to urge the end effector elements toward each other.

According to yet another aspect, a minimally invasive surgical instrument is provided which includes a pair of end effector mounting formations each of which is arranged to carry an end effector element and to be displaceable so that the end effector elements move toward and away from each other in a plane of movement. The instrument may include an urging arrangement arranged to urge the end effector elements toward each other when they are moved apart beyond a predetermined amount. The urging arrangement may include at least one resilient member, the resilient member being made from a nickel and titanium alloy.

According to a further aspect, a minimally invasive surgical instrument is provided which includes a pair of blade members arranged to be displaceable against each other to perform a cutting action. The instrument may further include at least one mechanical urging member for urging at least one blade against the other whilst the blades perform the cutting action.

The blade members may be connected together about a common pivotal connection. The mechanical urging member may include at least one resilient urging member extending from the pivotal connection to a position against one of the blade members, at which position the urging member urges that blade member in a lateral direction against the other blade member.

According to yet another aspect, a minimally invasive surgical instrument is provided which includes an elongate shaft defining a working end. It may further include a wrist member, one end of which is pivotally mounted on the working end of the shaft by means of a pivotal connection to enable the wrist member to pivot about the pivotal connection. At least one remote actuator operatively connected to the wrist member may be provided to cause the wrist member to pivot in response to actuation of the actuator. It may further include an end effector mounting formation on an opposed end of the wrist member. The end effector mounting formation may be arranged removably to hold an end effector.

According to yet a further aspect, a minimally invasive surgical instrument is provided which includes a pair of end effector elements defining free ends arranged to be displaceable toward and away from each other in a plane of movement. At least one of the end effector elements may converge toward the other in a direction in the plane of movement such that when the free ends abut a space extends between the end effector elements and inwardly of their abutting free ends. At least one of the end effector elements may be of a resilient material so that upon the application of increasing force urging the end effector elements toward each other whilst their free ends abut, the resilient end effector element is caused to deform resiliently so as to decrease a size of the space.

According to yet another aspect, a minimally invasive surgical instrument is provided which includes an elongate shaft defining a working end and an electrode mounting formation on which an electrode is mounted or removably mountable. An electrical conductor may be electrically connected to the electrode mounting formation. The conductor may extend from the electrode mounting formation in a direction toward an opposed end of the shaft. A wrist member one end of which is pivotally mounted, by means of a pivotal connection, on the working end of the shaft so as to enable angular displacement of the wrist member about the pivotal connection may further be provided. The electrode mounting formation may be positioned at an opposed end of the wrist member. The wrist member may be of an electrically insulative material.

According to yet a further aspect, a minimally invasive surgical instrument is provided which includes an elongate shaft defining a working end. It may further include an electrode mounting formation on which an electrode is mounted or removably mountable. An electrical conductor may be electrically connected to the electrode mounting formation. The conductor may extend from the electrode mounting formation in a direction toward an opposed end of the shaft. A wrist member may be provided, the wrist member having one end pivotally mounted, by means of a pivotal connection, on the working end of the shaft so as to enable angular displacement of the wrist member about the pivotal connection. The electrode mounting formation may be positioned at an opposed end of the wrist member. At least one elongate element may be operatively connected to the wrist member to cause angular displacement of the wrist member about the pivotal connection in response to pulling the elongate element. The elongate element may extend from the wrist member toward the opposed end of the shaft. The elongate element may be at least partially of an electrical insulative material.

According to another aspect, an end effector arrangement of a minimally invasive surgical instrument is provided which includes a pulley portion. A channel formation may extend at least partially circumferentially around the pulley portion. The channel formation may define opposed flange formations. One of the flange formations may have a diameter less than the other.

According to a further aspect, a minimally invasive surgical instrument is provided which includes a shaft having a working end. It may further include a wrist member mounted on the working end of the shaft. The wrist member may be arranged to have at least one degree of freedom of movement. At least one elongate element operatively connected to the wrist member to cause movement of the wrist member in response to pulling of the elongate element may be provided. The elongate element may have a relatively bendable portion in a region of the wrist member, and a relatively rigid portion in a region of the shaft.

According to yet a further aspect, a minimally invasive surgical instrument is provided which includes a shaft having a working end. An end effector mounting formation may be positioned at the working end of the shaft. It may be arranged to be angularly displaceable about at least two axes. Elongate elements may be connected to the end effector mounting formation to cause selective pivotal movement of the end effector mounting formation about the axes in response to selective pulling of the elongate elements. A support base may be positioned on an opposed end of the shaft. At least three spools may be angularly displaceably mounted on the support base. Opposed ends of the elongate elements may be connected to the spools so that selective angular displacement of the spools causes the selective pulling of the elongate elements. The spools may have axes that are parallel and spaced apart relative to each other.

The support base may include a generally planar outer surface and the axes may be generally perpendicular relative to the generally planar surface.

BRIEF DESCRIPTION OF THE DRAWINGS

The invention will now be described, by way of example, and with reference to the accompanying diagrammatic drawings, in which:

FIG. 5 shows a three-dimensional view, at an enlarged scale, of a wrist mechanism in accordance with a preferred embodiment of the invention;

FIG. 6 shows a side view of the wrist mechanism shown in FIG. 5 along arrow VI;

FIG. 7 shows an end view of the wrist mechanism shown in FIG. 5 along arrow VII;

FIG. 17 shows a side view of another wrist mechanism in accordance with a preferred embodiment of the invention;

FIG. 18 shows an end view in the direction of arrow XVIII in FIG. 17;

FIG. 19 shows a sectional view of the wrist mechanism along arrows A—A in FIG. 18;

DESCRIPTION OF THE SPECIFIC EMBODIMENTS

Figure 1:
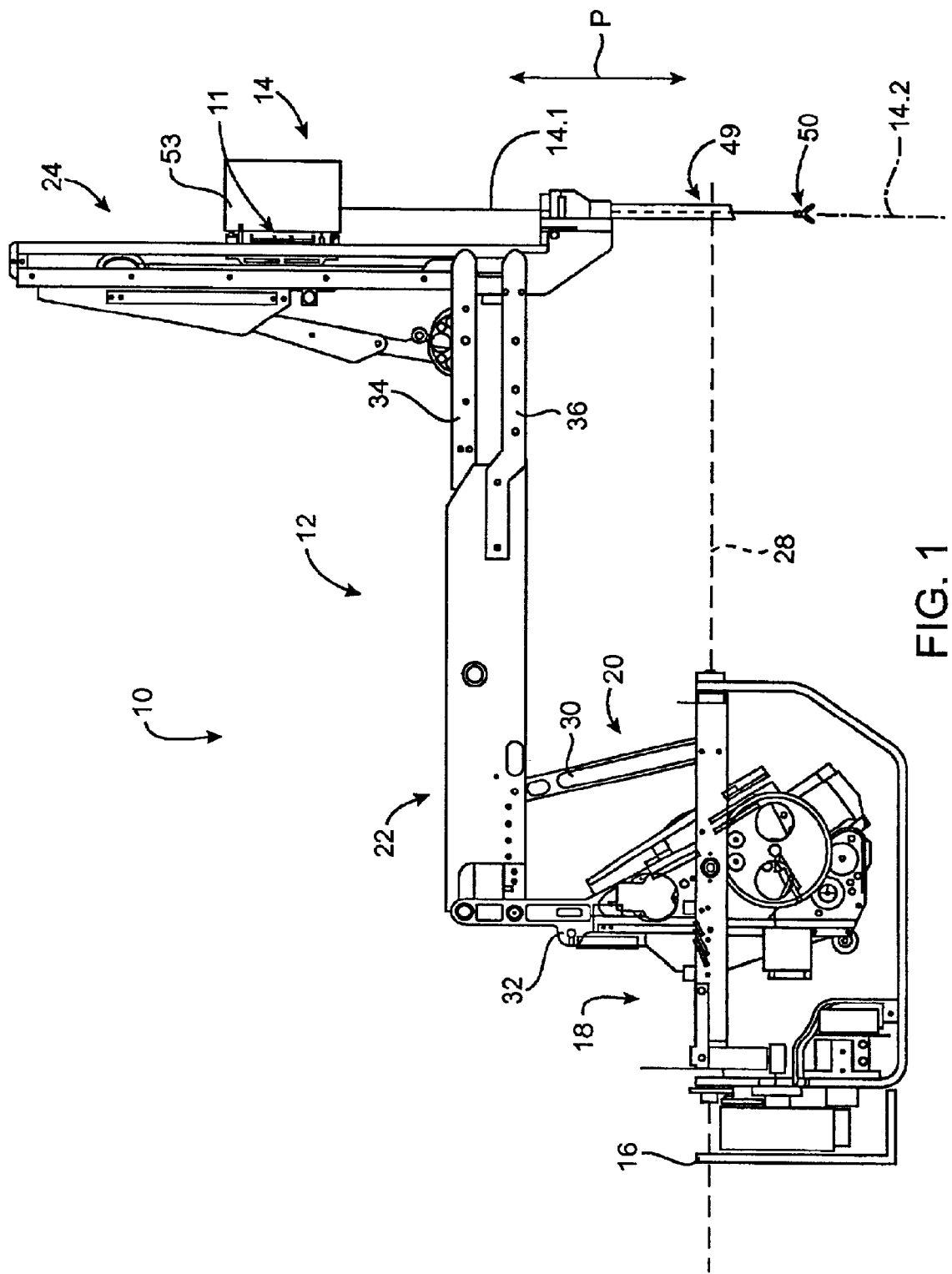
FIG. 1 shows a side view of a robotic arm and surgical instrument assembly in accordance with a preferred embodiment of the invention.
Figure 2:
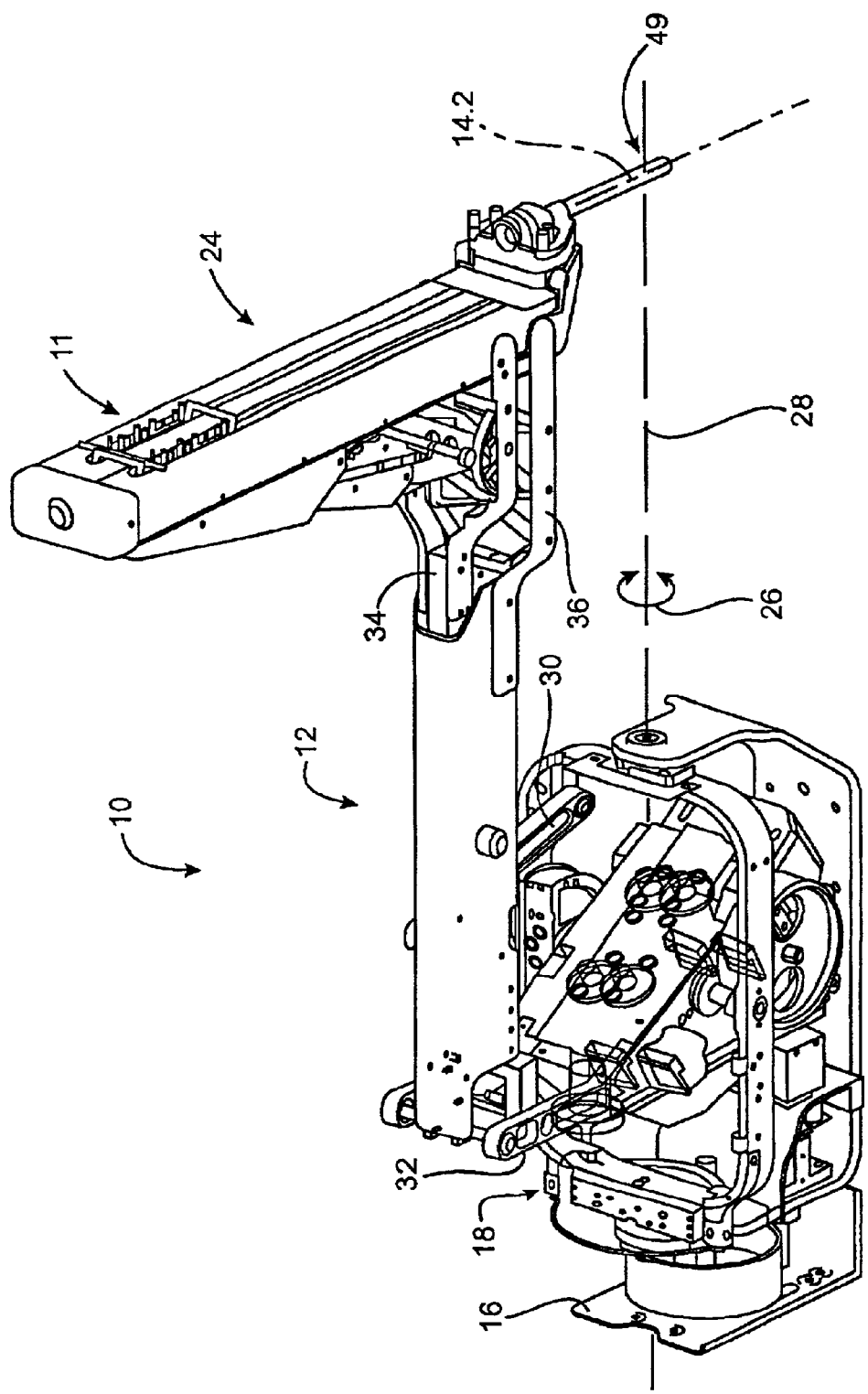
FIG. 2 shows a three-dimensional view corresponding to FIG. 1.

Referring to FIGS. 1 and 2 of the drawings, a robotic arm and surgical instrument assembly of a preferred embodiment of the invention is generally indicated by reference numeral 10.

Figure 3:
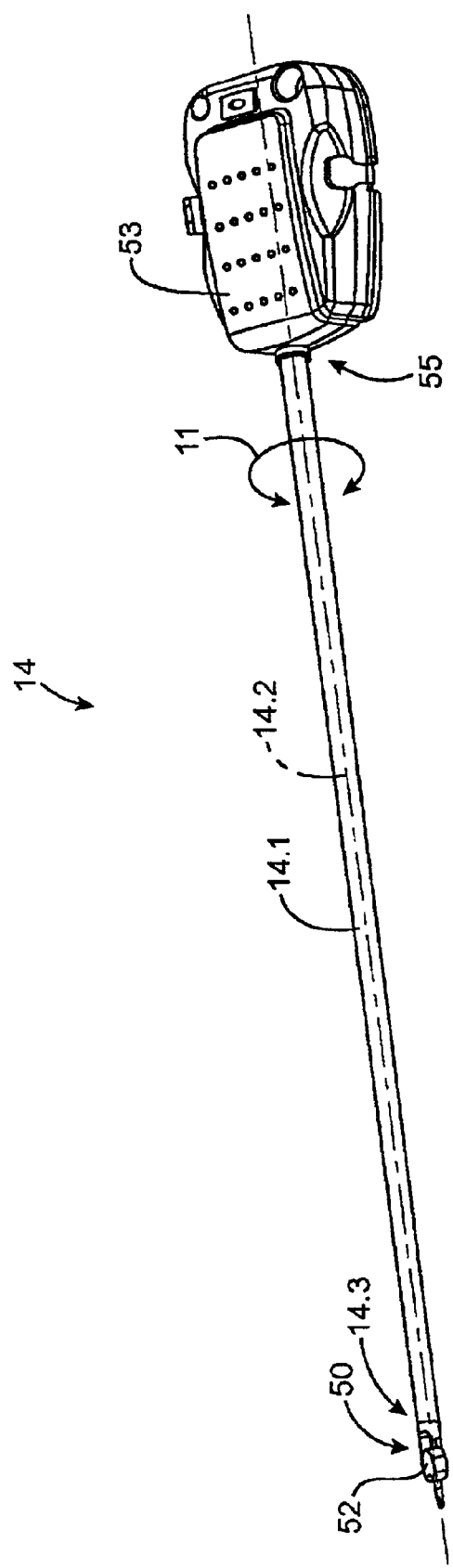
FIG. 3 shows a three-dimensional view of a surgical instrument of a preferred embodiment of the invention.

The assembly 10 includes a robotic arm, generally indicated by reference numeral 12. It further includes a surgical instrument schematically and generally indicated by reference numeral 14 in FIG. 1. FIG. 3 indicates the general appearance of the surgical instrument 14.

The surgical instrument 14 includes an elongate shaft 14.1. A wrist-like mechanism, generally indicated by reference numeral 50, is located at a working end of the shaft 14.1. A housing 53 arranged releasably to couple the instrument 14 to the robotic arm 12, is located at an opposed end of the shaft 14.1. In FIG. 1, and when the instrument 14 is coupled or mounted on the robotic arm 12, the shaft 14.1 extends along an axis indicated at 14.2. The instrument 14 is typically releasably mounted on a carriage 11 that is driven to translate along a linear guide formation 24 in the direction of arrows The surgical instrument 14 is described in greater detail herein below.

The robotic arm 12 is typically mounted on a base (not shown) by means of a bracket or mounting plate 16. The base is typically in the form of a mobile cart or trolley (not shown) which is retained in a stationary position during a surgical procedure.

The robotic arm 12 includes a cradle, generally indicated at 18, an upper arm portion 20, a forearm portion 22 and the guide formation 24. The cradle 18 is pivotally mounted on the plate 16 gimbaled fashion to permit rocking movement of the cradle in the direction of arrows 26 as shown in FIG. 2, about a pivot axis 28. The upper arm portion 20 includes link members 30, 32 and the forearm portion 22 includes link members 34, 36. The link members 30,32 are pivotally mounted on the cradle 18 and are pivotally connected to the link members 34, 36. The link members 34, 36 are pivotally connected to the guide formation 24. The pivotal connections between the link members 30, 32, 34, 36, the cradle 18, and the guide formation 24 are arranged to enable the robotic arm to move in a specific manner. The movement of the robotic arm is illustrated schematically in FIG. 4.

Figure 4:
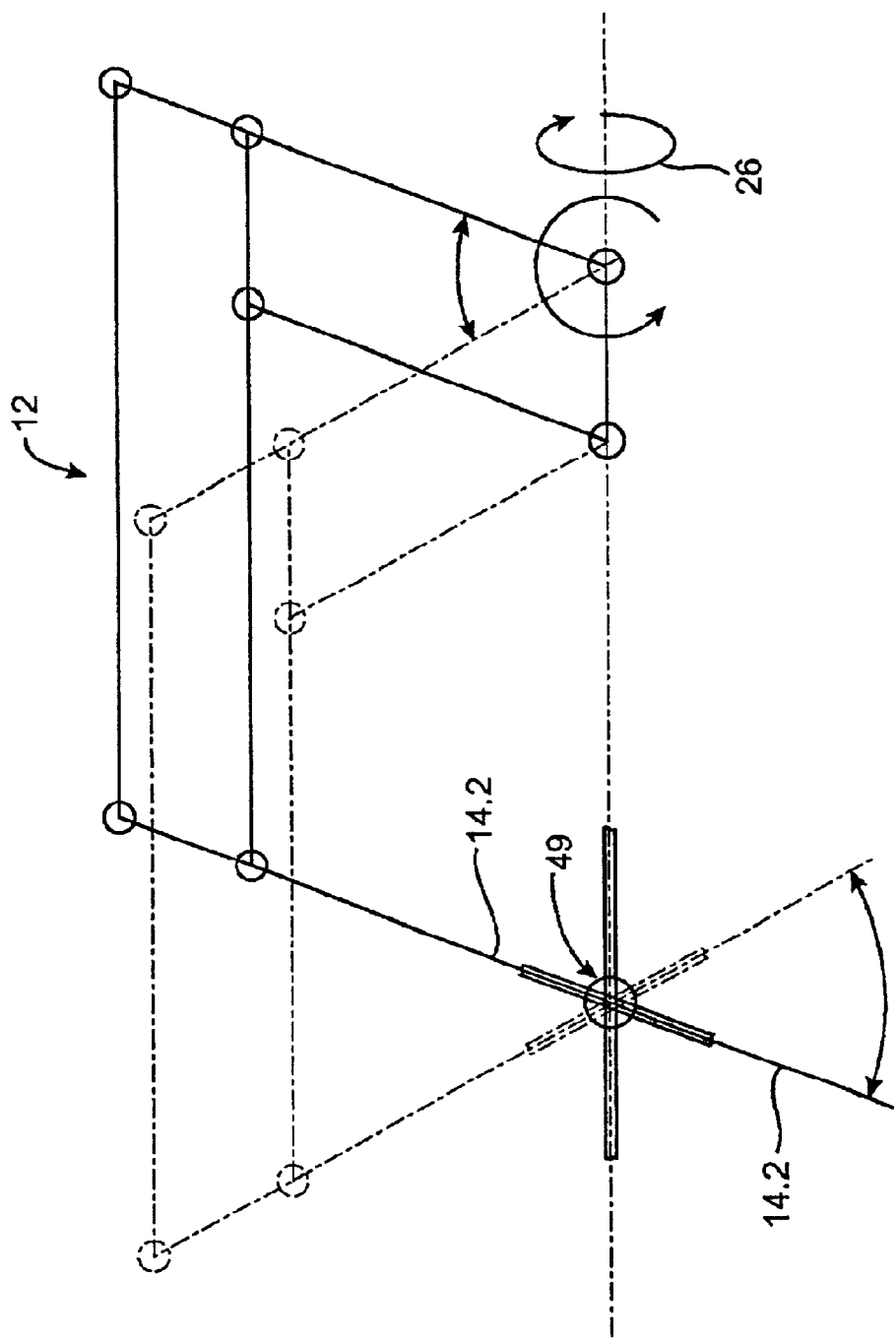
FIG. 4 shows a schematic diagram corresponding to a side view of the robotic arm shown in FIG. 1 and indicates the arm having been displaced from one position into another position.

With reference to FIG. 4, the solid lines schematically indicate one position of the robotic arm and the dashed lines indicate another possible position into which the arm can be displaced from the position indicated in solid lines.

It will be understood that the axis 14.2 along which the shaft 14.1 of the instrument 14 extends when mounted on the robotic arm 12 pivots about a pivot center or fulcrum 49. Thus, irrespective of the movement of the robotic arm 12, the pivot center 49 remains in the same position relative to the stationary base on which the arm 12 is mounted. In use, the pivot center 49 is positioned at a port of entry into a patient's body when an internal surgical procedure is to be performed. It will be appreciated that the shaft 14.1 extends through such a port of entry, the wrist-like mechanism 50 then being positioned inside the patient's body. Thus, the general position of the mechanism 50 relative to the surgical site in a patient's body can be changed by movement of the arm 12. Since the pivot center 49 is coincident with the port of entry, such movement of the arm does not excessively effect the surrounding tissue at the port of entry. It is to be appreciated that the field of application of the invention is not limited to surgical procedures at internal surgical sites only, but can be used on open surgical sites as well. Nor should the invention be understood to be limited to a remote center-of-motion apparatus, such as depicted in FIG. 4, but can be useful in other manners of delivering a robotic surgical tool to a target site, such as computed or natural centers-of-motion robotic arms.

Referring now to FIGS. 5, 6 and 7 of the drawings, the wrist-like mechanism 50 in accordance with the invention, will now be described in greater detail. In FIG. 5, the working end of the shaft 14.1 is indicated at 14.3. The wrist-like mechanism 50 includes a rigid wrist member 52. One end portion of the wrist member 52 is pivotally mounted in a clevis, generally indicated at 17, on the end 14.3 of the shaft 14.1 by means of a pivotal connection 54. As can best be seen in FIG. 7 of the drawings, it will be appreciated that the wrist member 52 can pivot in the direction of arrows 56 about the pivotal connection 54. An end effector, generally indicated by reference numeral 58, is pivotally mounted on an opposed end of the wrist member 52. The end effector 58 is in the form of a clip applier for anchoring clips during a surgical procedure. Accordingly, the depicted end effector 58 has two parts 58.1, 58.2 together defining a jaw-like arrangement. It will be appreciated that the end effector can be in the form of any required surgical tool having two members or fingers which pivot about a common pivotal axis, such as scissors, pliers for use as needle drivers, or the like.

The end effector 58 is pivotally mounted in a clevis, generally indicated by reference numeral 19, on an opposed end of the wrist member 52, by means of a pivotal connection 60. It will be appreciated that free ends 11, 13 of the parts 58.1, 58.2 are angularly displaceable about the pivotal connection 60 toward and away from each other as indicated by arrows 62, 63 in FIG. 6. It will further be appreciated that the members 58.1, 58.2 can be displaced angularly about the pivotal connection 60 to change the orientation of the end effector 58 as a whole, relative to the wrist member 52. Thus, each part 58.1, 58.2 is angularly displaceable about the pivotal connection 60 independently of the other, so that the end effector 58 is, as a whole, angularly displaceable about the pivotal connection 60, as indicated in dashed lines in FIG. 6. The axes represented by pivotal connections 54 and 60 are preferably offset to make the wrist unit as a whole of as small a profile as possible, thereby to minimize the size of puncture wound necessary for the tool/wrist combination to enter a patient's body.

Figure 8:
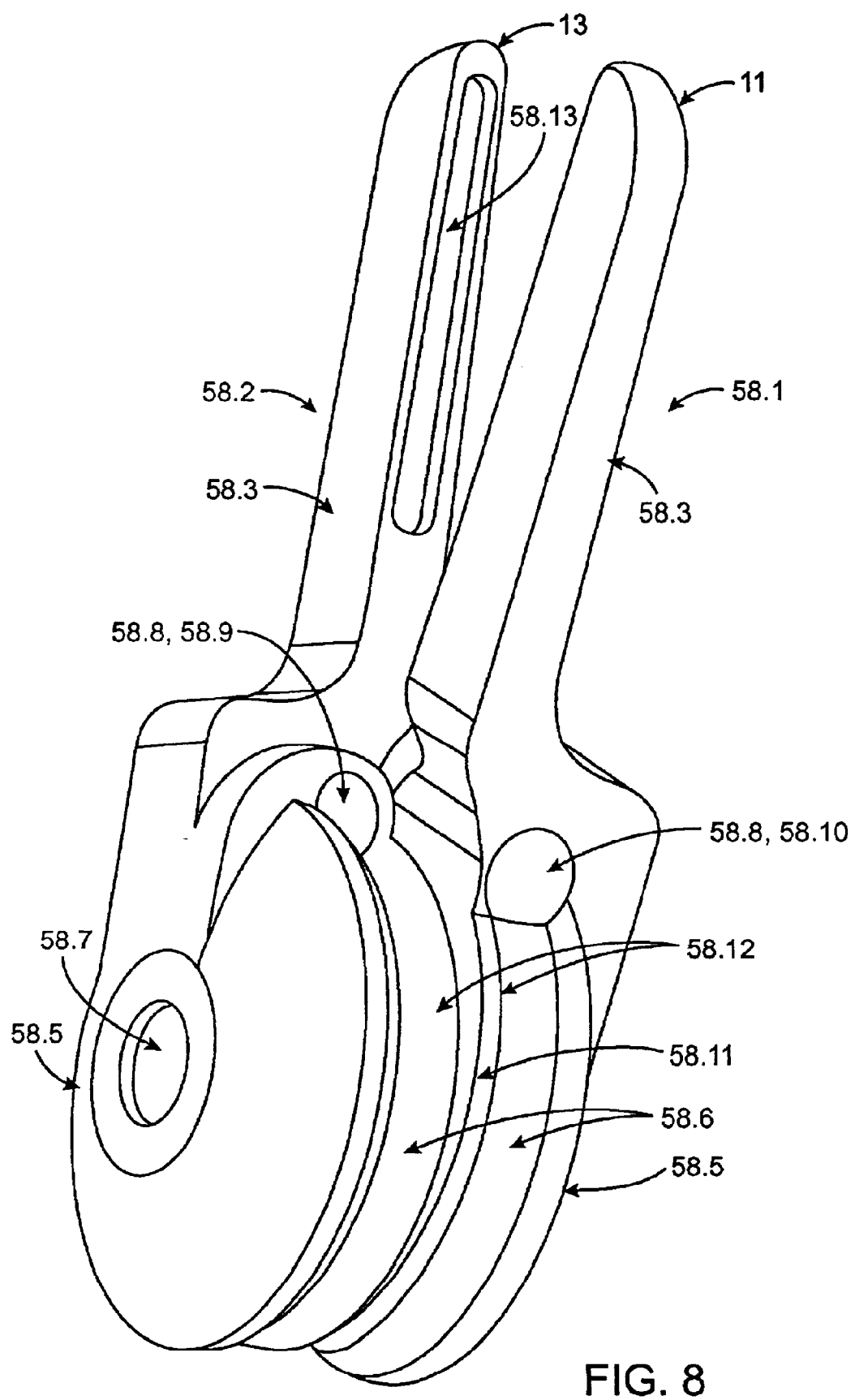
FIG. 8 shows, at an enlarged scale, a clip applier end effector in accordance with a preferred embodiment of the invention.
Figure 9:
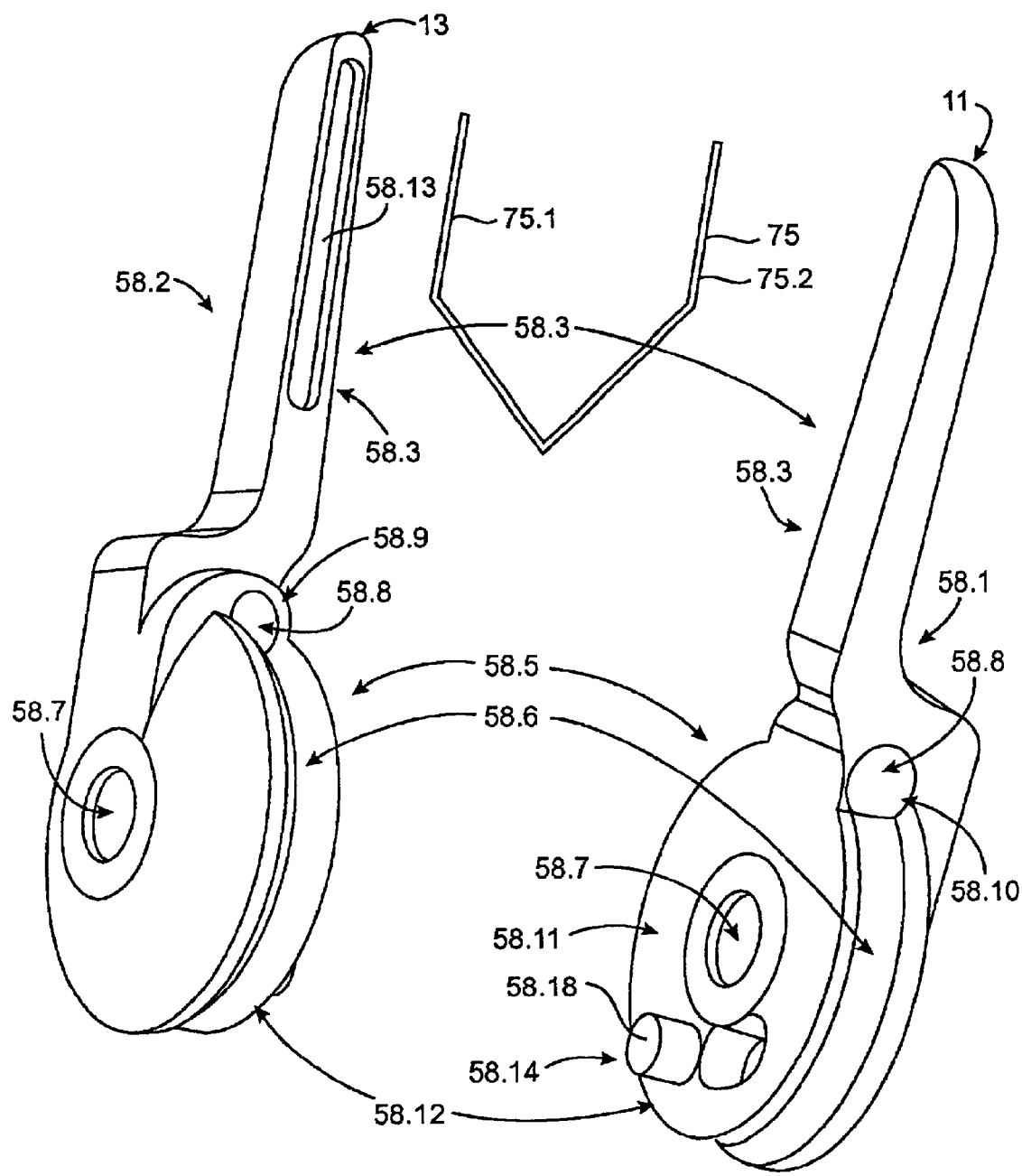
FIG. 9 shows an exploded view of the clip applier end effector shown in FIG. 8.

The end effector 58 will now be described in greater detail with reference to FIGS. 8 and 9. The parts 58.1, 58.2 are the same. They are the same so as to keep production costs low. Accordingly, the parts 58.1, 58.2 each include an elongate finger portion or end effector element 58.3. The finger portion 58.3 is integrally formed with an end effector mounting formation in the form of, e.g., a pulley portion 58.5. The pulley portion 58.5 defines a circumferentially extending channel 58.6 in which an elongate element in the form of, e.g., an activation cable, is carried, as described in greater detail herein below.

The pulley portion 58.5 includes an axially-extending, centrally-disposed hole 58.7 through which a pivot pin of the pivotal connection 60 extends. A generally circumferentially directed hole 58.8 extends through a nape region of the finger portion 58.3 and generally in register with the circumferentially extending channel 58.6. The hole 58.8 has a first portion 58.9 and a second portion 58.10 having a diameter greater than the first portion 58.9. In use, the activation cable has a thickened portion along its length which seats in the hole portion 58.10, the rest of the activation cable then extending along the channel 58.6 in opposed directions. The thickened portion is crimped in its seated position in the hole portion 58.10 so as to anchor the cable in the hole 58.8. It will be appreciated that a greater force is necessary to clamp the free ends together when gripping an object therebetween, than that which is required to open the free ends 11, 13. Thus, the thickened portion of the cable is urged against an annular stepped surface between the hole portion 58.9 and the hole portion 58.10, when the free ends 11, 13 are urged into a closed condition.

The part 58.1, 58.2 has an operatively inwardly directed face 58.11 that rides against the face 58.11 of the other one of the parts 58.1, 58.2.

As can best be seen with reference to FIG. 6, the wrist member 52 is flanked by two sets of pulleys 64, 66 which are coaxially positioned on the pivotal connection 54 and in the clevis 17 at the end 14.3 of the shaft 14.1. Two further sets of pulleys 68, 70 are rotatably mounted on opposed sides of the wrist member 52. Each pulley of the set of pulleys 68 on the one side of the wrist member 52 is generally co-planar with an associated pulley of the pulley set 66. Furthermore, each of the pulleys 68 is positioned such that its circumference is in close proximity to the circumference of its associated pulley of the pulley set 66. A similar arrangement exists for each pulley of the pulley set 70 on the other side of the wrist member and its associated pulley of the pulley set 64.

Thus, the circumferentially extending channel formation of each pulley of the pulley sets 68, 70 and their associated pulleys of the pulley sets 64, 66 define between each of them a space 72 through which an activation cable, as described in greater detail herein below, can snugly pass.

Figure 10:
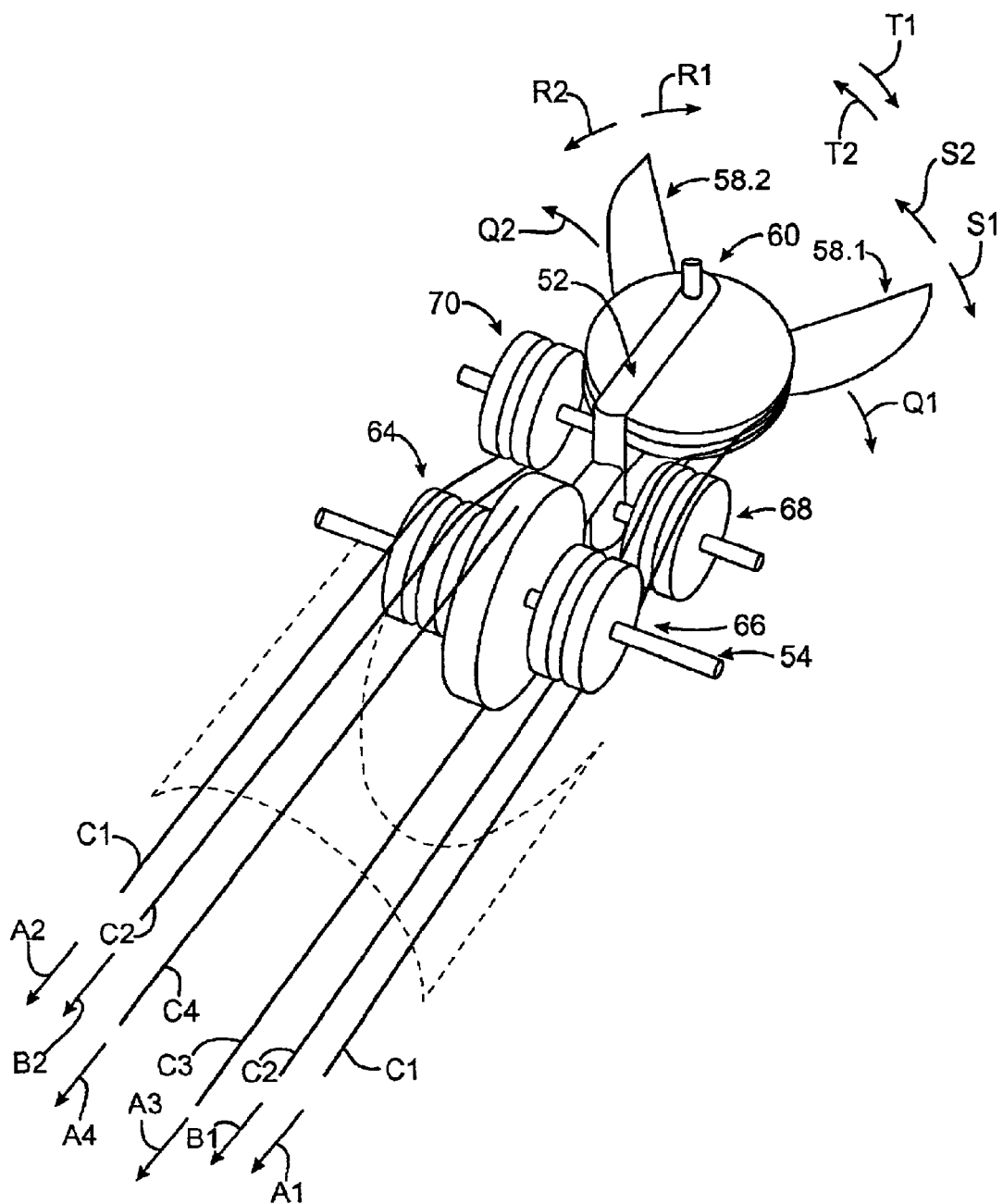
FIG. 10 shows a three-dimensional schematic view of the wrist mechanism shown in FIGS. 5, 6 and 7.

The operation of the wrist-like mechanism will now be described for the two-fingered arrangement depicted in FIGS. 5 to 7, with reference to the schematic representation of the wrist mechanism shown in FIG. 10. In FIG. 10, four elongate elements, e.g., cables, are used to effect movement of the wrist mechanism 50. These cables are indicated at C1, C2, C3 and C4. It will be appreciated that six cable lengths extend from the wrist-like member, although fewer cable lengths would be required for a single-finger end effector. Four of these cable lengths are defined by two cables C1 and C2, each of which is anchored on one of the parts 58.1, 58.2, respectively. Naturally, six separate cable lengths can be used instead. In such a case, an end of each of such a cable length is appropriately anchored to enable angular displacement of the parts 58.1, 58.2 about their pivotal connections 60 and of the wrist member 52 about its pivotal connection 54.

Cable C1 rides over an outer pulley of the pulley set 64, an outer pulley of the pulley set 70, over part of circumferential channel 58.6 of the pulley portion 58.5 of the part 58.2 of the end effector 58, through the hole 58.8 (not shown in FIG. 10), again along part of the circumferential channel 58.6 of the pulley portion 58.5, over an outer pulley of the pulley set 68 and over an outer pulley of the pulley set 66. Similarly, cable C2 rides over an inner pulley of the pulley set 64, over an inner pulley of the pulley set 70, along the circumferential channel 58.6 of the part 58.1 of the end effector 58, through the hole 58.8 of the part 58.1, again along the circumferential channel 58.6 of the pulley portion 58.5, over an inner pulley of the pulley set 68 and over an inner pulley of the pulley set 66.

In use, when cable C1 is pulled in the direction of arrow A1 the part 58.2 of the end effector is caused to displace angularly about the pivotal connection 60 in the direction of arrow R1. Similarly, if the cable C1 is pulled in the direction of arrow A2, the part 58.2 is caused to displace angularly about the pivotal connection 60 in the direction of arrow R2. As discussed earlier, the cables C1, C2 are anchored in the holes 58.8 in the respective parts 58.1, 58.2 of the end effector 58. When cable C2 is pulled in the direction of arrow B1, the other part 58.1 of the end effector 58 is caused to displace angularly about 60 in the direction of arrow S1. Naturally, when the cable C2 is pulled in the direction of arrow B2 the part 58.1 is caused to displace in the direction of arrow S2.

It will be appreciated that to cause the part 58.2 to be angularly displaced toward the part 58.1 simultaneously with the part 58.1 toward the part 58.2, cable C1 is pulled in the direction of arrow A1 and the cable C2 is pulled in the direction of arrow B2 simultaneously.

Furthermore, to vary the orientation of the end effector 58 as a whole relative to the wrist member 52, as indicated in FIG. 6, cable C2 is pulled in the direction of arrow B1 simultaneously with the cable C1 in the direction of arrow A1 so as to displace both parts 58.1, 58.2 in the direction of arrow T1. Similarly, to move the end effector in the direction of arrow T2, both cables C and C2 are pulled simultaneously in the direction of arrows A2, B2, respectively.

The cables C1, C2, C3, C4, at least in the region of the wrist member, are typically made of Tungsten or stainless steel to provide sufficient strength, bendability and durability.

Referring to FIG. 6 of the drawings, the wrist member 52 includes a passage 80 extending therethrough. The passage 80 is arranged to receive activation cables therein from opposed sides and to engage free ends of the cables. The activation cables correspond to cables C3 and C4 in FIG. 10 of the drawings. The free ends of each of the cables carries a thickened end portion. Thus, on each side of the wrist member, a seat 84 is provided in which the thickened end of the cable is received. It will be appreciated that the cables are positioned in place by passing the ends of the cables that are not thickened, through the passage 80 from opposed sides. Once the cables are threaded through the passage 80, the thickened ends engage in the opposed seats 84. The cables extend from the seats 84, through the passage 80, and along guide channels 86 extending from the passage 80 downwardly along each opposed side of the wrist member 52. The cables C3, C4 each then pass through one of the holes 47, as indicated in FIG. 5 of the drawings, in a base region of the clevis 17 toward the opposed end of the shaft 14.1. It will be appreciated that each of the cables C1, C2, C3 and C4 pass from the wrist mechanism 50 through appropriately positioned holes 47 in the base region of the clevis 17, and internally along the shaft, toward the housing 53. Holes 47 should be appropriately sized to minimize leakage of insufflation gas, such as carbon dioxide, from the patient's cavity during the surgical procedure. Clearances of no more than about several thousandths of an inch around the cable have proven satisfactory.

Figures 11A, 11B:
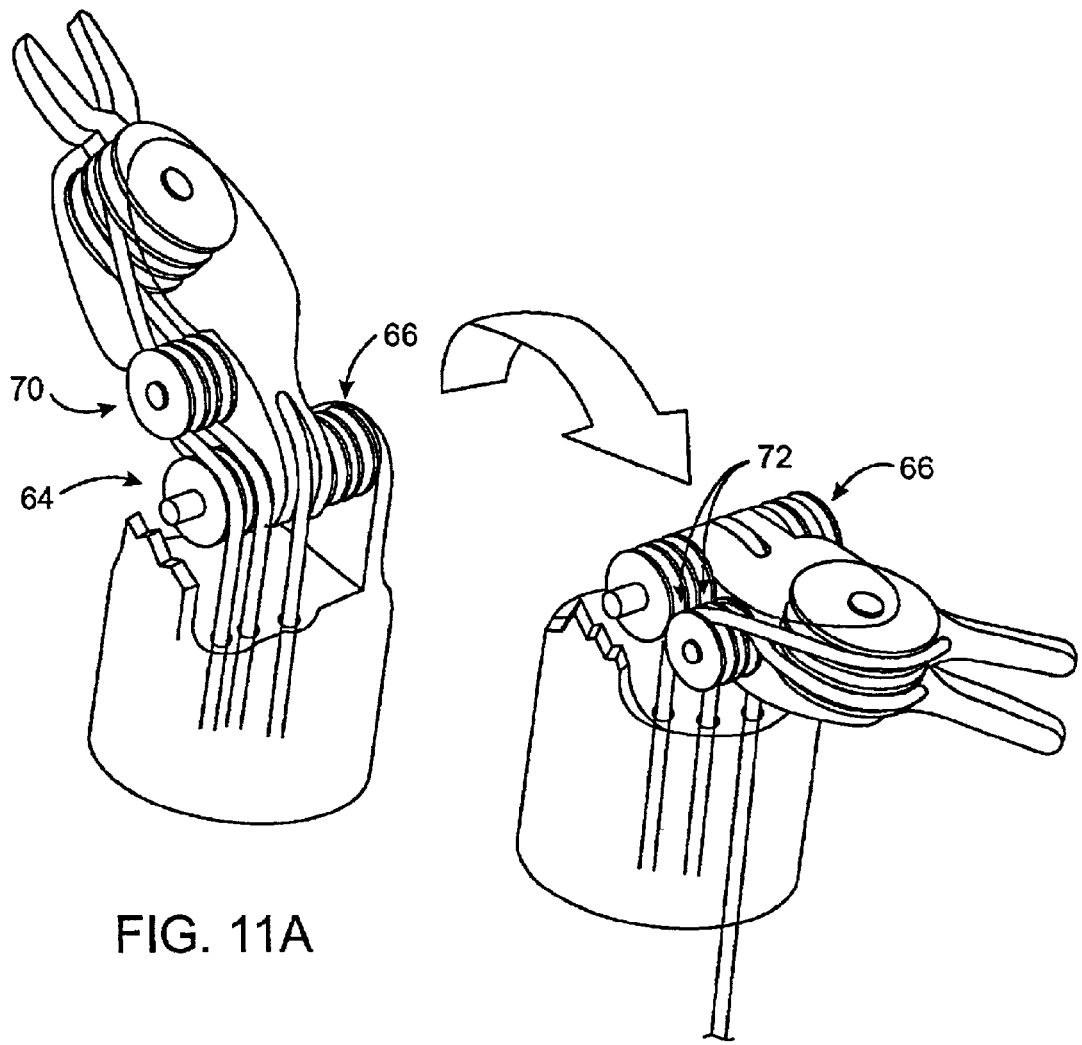
FIGS. 11A and 11B show three-dimensional schematic views of the wrist mechanism shown in FIGS. 5, 6 and 7, and indicates pivoting of a wrist member of the wrist mechanism about a pivotal connection.
Figure 12:
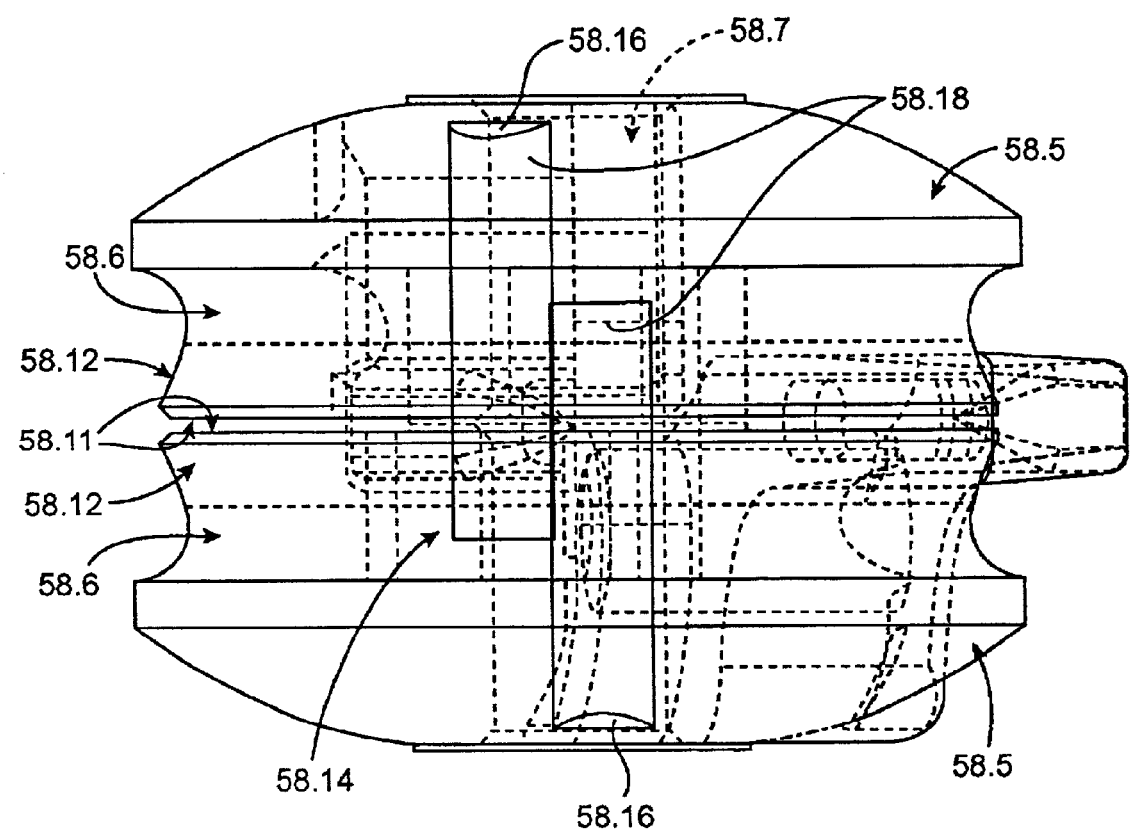
FIG. 12 shows a sectional view of the clip applier shown in FIGS. 8 and 9 in the direction of arrow XII in FIG. 13.
Figure 13:
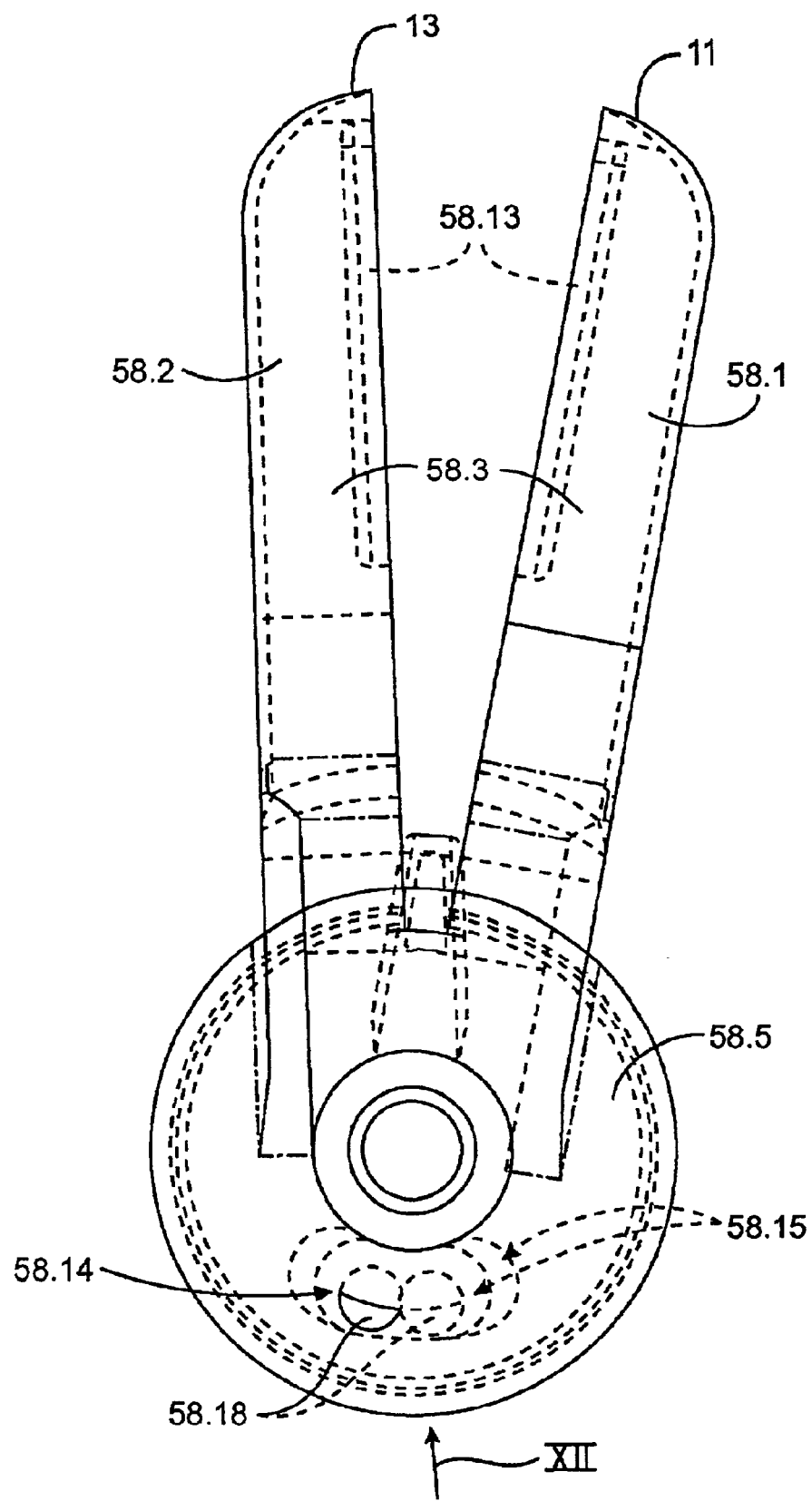
FIG. 13 shows, at a diminished scale, a plan view of the clip applier shown in FIG. 12.
Figure 14:
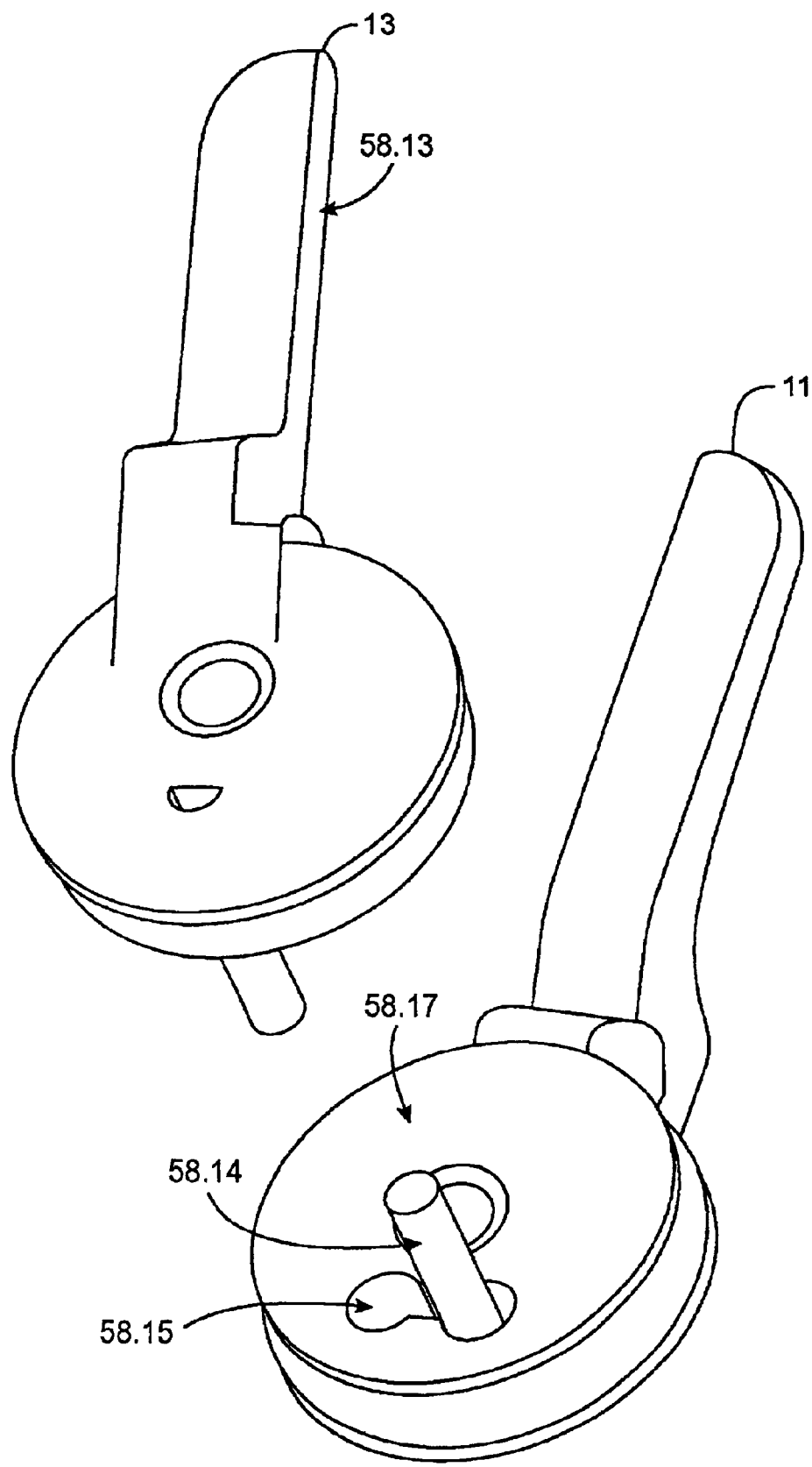
FIG. 14 shows another three-dimensional view of the clip applier shown in FIGS. 8 and 9, and indicates urging means for urging finger portions of the clip applier toward each other when the finger portions are angularly displaced beyond a predetermined position relative to each other.

Referring once again to FIG. 10, the cables secured in the passage 80 and which extend along the shaft 14.1 are represented by C3 and C4. It will be appreciated that when cable C3 is pulled in the direction of arrow A3, the wrist member is angularly displaced about the pivotal connection 54 in the direction of arrow Q1. Similarly, when the cable C4 is pulled in the direction of arrow A4, the wrist member is angularly displaced about the connection 54 in the direction of arrow Q2. The pivoting action of the wrist member 52 in response to the selective pulling of the cables C3, C4 is shown schematically in FIGS. 11A and 11B. It will be appreciated that the pulley sets 64 and 70, 66 and 68 are in close proximity to each other so as to define the snug passages 72 thereby to inhibit the cables riding off of the pulleys during the pivoting motion as indicated in FIGS. 11A and 11B.

Referring to FIG. 7 of the drawings, it will be seen that where the cables C1, C2 extend from the pulley portions 58.5 of the parts 58.1, 58.2, as indicated at 79, to the pulleys of the pulley set 68, the cables C1, C2 are not aligned with the circumferentially extending channels of the pulley portions 58.5. To inhibit wear on the cables C1, C2, operatively inner flanges of the pulley portions 58.5 are rounded and have a lesser outer diameter than the outer flanges. This can be seen most clearly in FIGS. 8 and 9, and as indicated by reference numeral 58.12. In addition, to avoid premature wear on the cables, the preferred travel path, e.g., for the high-tension cable operative to close a finger member in a dual jaw arrangement should minimize the fleet angle, as shown best in FIGS. 10 and 11.

As can be seen with reference to FIG. 3, the shaft 14.1 is rotatably coupled to the housing 53 at 55 to enable angular displacement of the shaft 14.1 relative to the housing 53 as indicated by arrows H. The shaft 14.1 is hollow and the cables C1, C2, C3 and C4 extend axially along and inside the shaft to driving members in the form of spool assemblies (not shown in FIG. 3) in the housing 53.

Figure 22:
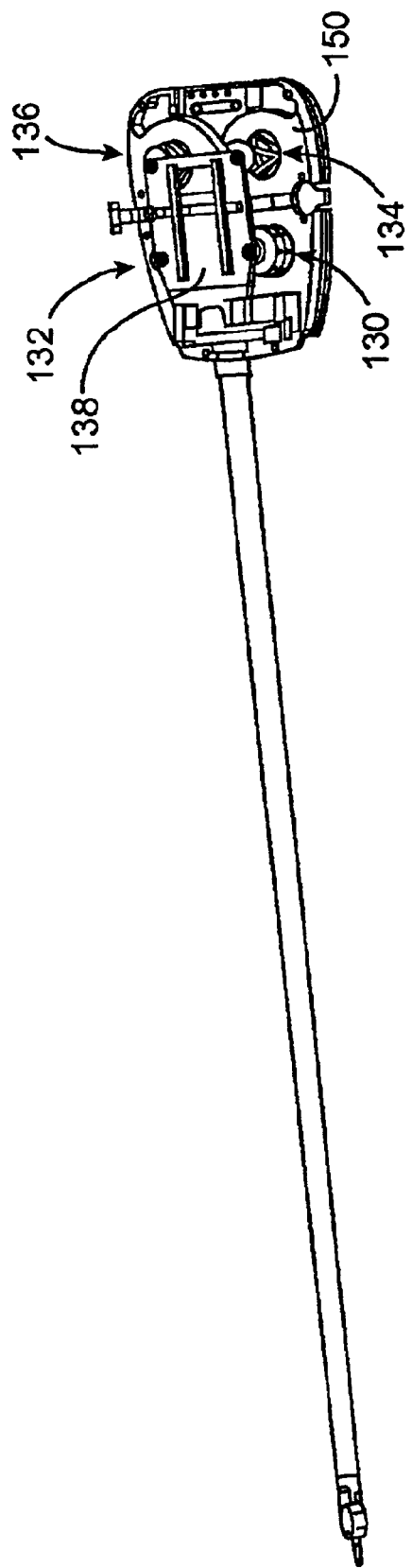
FIG. 22 shows a three-dimensional view of the surgical instrument shown in FIG. 3, a housing cover of a housing of the instrument having been removed to show working elements inside the housing.
Figure 23:
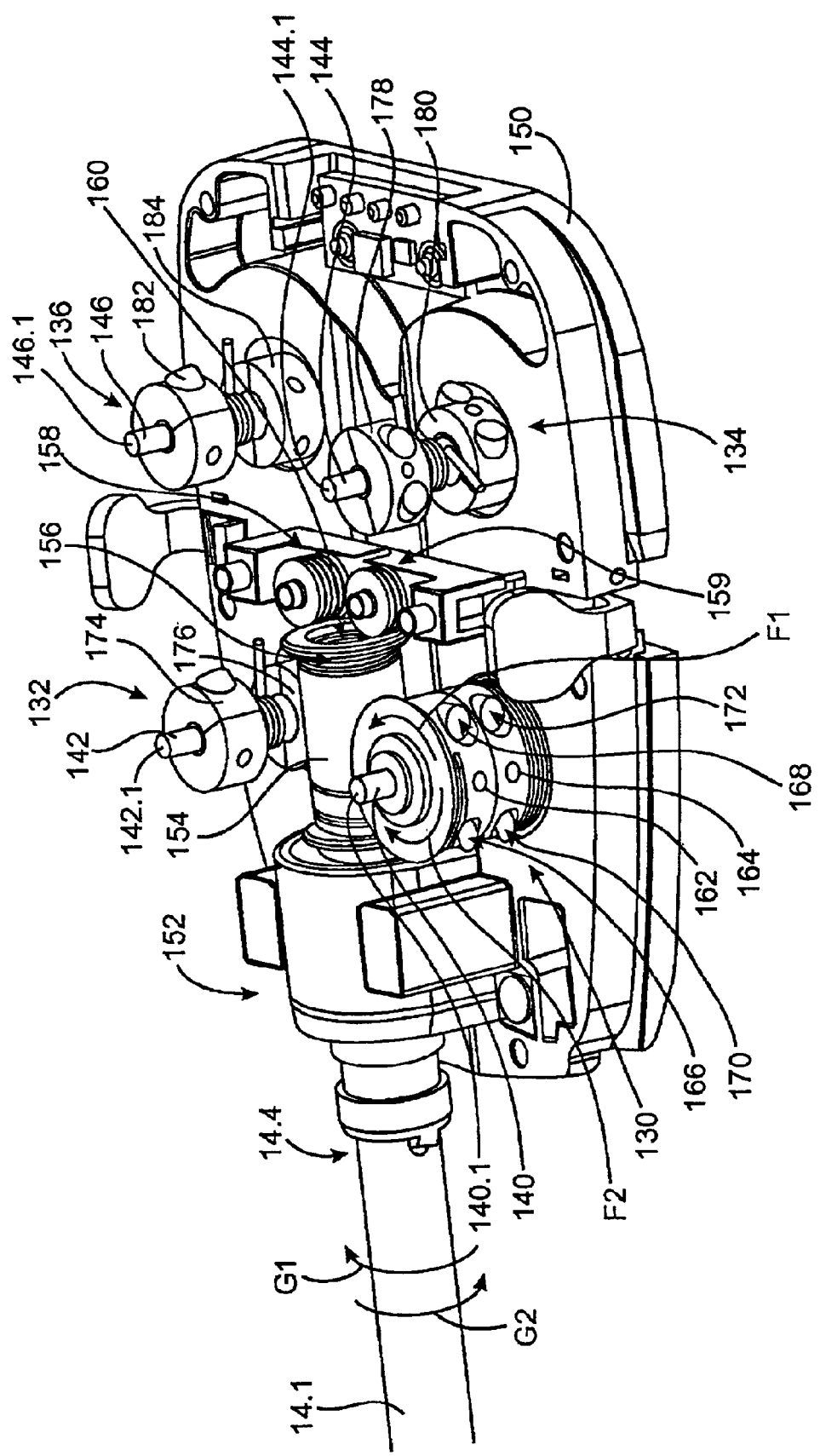
FIG. 23 shows, at an enlarged scale relative to FIG. 22, a three-dimensional view of the working elements in the housing.
Figure 24:
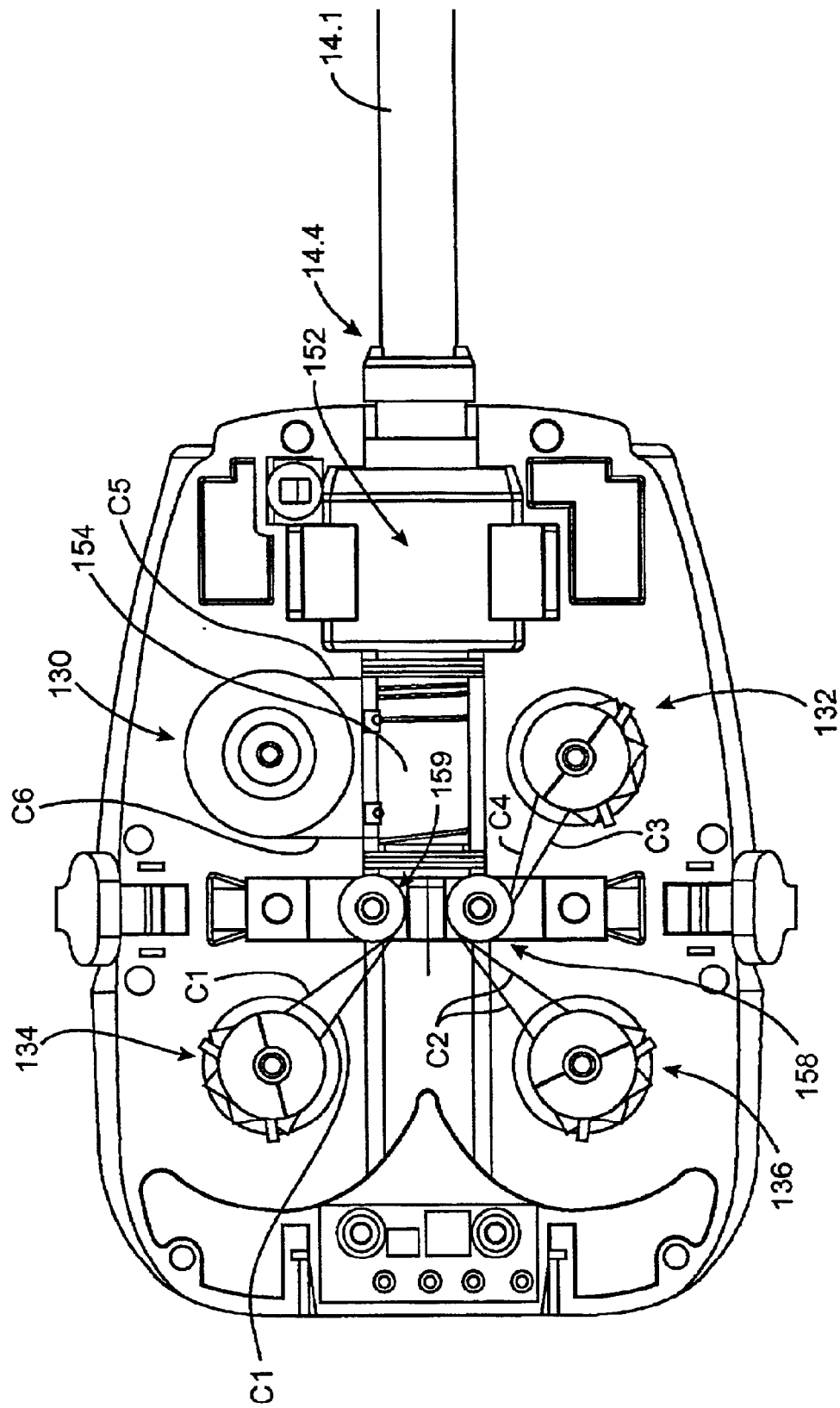
FIG. 24 shows a plan view corresponding to FIG. 23.

Referring now to FIGS. 22, 23 and 24 of the drawings, the spools are generally indicated by reference numerals 130, 132, 134 and 136, respectively. The spools 130, 132, 134 and 136 are secured on shafts 140, 142, 144 and 146, respectively. The shafts 140, 142, 144, 146 extend through a base 150 of the housing 53. Ends, 140.1, 142.1, 144.1 and 146.1 of the shafts 140, 142, 144, 146 are rotatably held in a mounting plate 138 (only shown in FIG. 22). The mounting plate 138 has been removed in FIGS. 23 and 24 to show the spools 130, 132, 134 and 136 more clearly. Opposed ends of the shafts 140, 142, 144, 146 extend through the base 150 to an opposed side, hidden in FIGS. 22, 23, and 24. At the opposed side, each shaft 140, 142, 144, 146 carries an engaging member (not shown) on its opposed end. Each engaging member is arranged releasably to couple with a complementary engaging member rotatably mounted on the carriage 11, as can best be seen in FIGS. 1 and 2 of the drawings. The engaging members on the carriage 11 are operatively connected to actuators, e.g., electric motors (not shown), to cause selective angular displacement of each engaging member on the carriage in response to actuation of its associated actuator. Thus, selective actuation of the actuators is transmitted through the engaging members on the carriage 11, to the engaging members on the opposed ends of the shafts 140, 142, 144, 146 to cause selective angular displacement of the spools 130, 132, 134, 136.

An opposed end portion 14.4 of the shaft 14.1 is rotatably mounted on the base 150 in a bearing assembly 152. Furthermore, the opposed end portion 14.4 of the shaft 14.1 carries a drum 154 which intrudes into the housing 53 beyond the bearing assembly 152. Two elongate elements in the form of Tungsten cables C5, C6, as can best be seen in FIG. 24, extend between the drum 154 and the spool 130. It will be appreciated that ends of the cables C5, C6 are anchored on the spool 130 and opposed ends are anchored on the drum 154, opposed end portions of the cables C5, C6 being at least partially wrapped around the spool 130 and the drum 154, respectively. Accordingly, angular displacement of the spool 130 in the direction of arrow F1 causes angular displacement of the shaft in the direction of arrow G1, and likewise angular displacement of the spool 130 in the direction of arrow F2 cause angular displacement of the shaft in the direction of arrow G2.

The drum 154 and the spool 130 typically have circumferentially extending guide channels to guide wrapping of the cables C5, C6 thereon so as to inhibit the cables C5, C6 from riding over themselves or each other. The guide channels on the drum 154 are indicated by reference numeral 156. To ensure that the cable remains seated in its associated guide channel during wrapping/unwrapping around spool 130, the bottom of each groove preferably coincides with the overall outer diameter of the non-grooved portion of spool 130—rather than the groove being cut into the spool itself—with the edges of each groove raised off the surface of spool 130 to create a slightly increased outer diameter for the groove edges of grooved portion of spool 130. This construction is preferred to maintain an ordered wrapping of the cables around the spool during use.

Cables preferably are constructed from multiple braids of fine wire, to provide strength and resiliency. For strong, flexible cables, 150 to 350 braids of 0.0007 to 0.001 inch diameter tungsten wire have been used, providing cables with outer diameters of 0.014 to 0.018 inches. Cables with more braids, thicker wire, and or thicker overall diameter are more useful for tools that require more torque to function, such as the clip applier. Since manufactured and wound cables typically inherently include some "construction stretch," and since the sensitivity of the tools described herein is enhanced by minimizing the inherent stretch in the cables used, it is preferable to remove that construction stretch before use. Several steps may be taken to remove this stretch, including cycling cables through their range of movement, imparting greater-than-expected loads to the cables, and retensioning the cables to remove the stretch resulting from these steps.

Although the preferred embodiment of this invention is disclosed comprising cables, pulleys and spools, the particular arrangement of drive elements is not limiting to the scope of the present invention. For example, the present invention also encompasses other flexible and non-flexible drive elements such as rods, linkages, etc. which could be arranged to achieve the same functionality set forth herein.

Opposed ends of the cables C3, C4 are secured on the spool 132. From the spool 132, the cables C3, C4 are guided over two idler pulleys arranged one on top of the other at 158, and into a centrally disposed passage 160 extending through the drum 154 and into the hollow shaft 14.1. It will be appreciated that selective angular displacement of the spool 132 causes selective pulling of the cables C3, C4. Naturally selective angular displacement of the spool 132 is caused by an actuator, e.g., an electric motor, selectively driving an associated engaging member on the carriage 11 which selectively drives the engaging member on the opposed end of the shaft 142.

The cable portions C1, C1 are operatively connected to the spool 134 and extend from the spool 134 over a pair of guide pulleys 159 and through the passage 160 and internally along the shaft 14.1. The cable portions C2, C2 are operatively connected to the spool 136 and extend from the spool 136 over a pair of guide pulleys at 158 and through the passage 160 and internally along the shaft 14.1. Selective angular displacement of the spools 134, 136 is achieved in a similar fashion as the spools 130, 132, which in turn causes selective pulling of the cable portion C1, C1, C2, C2 in the direction of arrows A1, A2, B, B2 shown in FIG. 10.

A tensioning arrangement is provided on each spool 130, 132, 134, 136 to tension its associated cable lengths. The tensioning arrangement on the spool 130 includes two generally annular collar formations 162, 164. An end of the cable C5 is anchored on the annular collar 164, and, similarly, an end of the cable C6 is anchored on the annular collar 162. Each collar 162, 164 is releasably clamped on the shaft 140 by means of opposed screw threaded fasteners at 166, 168, 170, 172, respectively. To tension the cable C6, the screw threaded fasteners 166, 168 are loosened so as to release the clamping force of the annular collar 162 on the shaft 140, the annular collar 162 is then angularly displaced relative to the shaft 140 to tension the cable C6 and thereafter the annular collar 162 is re-clamped on the shaft by fastening the fasteners 166, 168. It will be appreciated that to tension the cable C5, the annular collar 164 is angularly re-positioned on the shaft 140 in similar fashion to the annular collar 162.

A similar tensioning arrangement is provided on each of the other spools 132, 134, 136. The annular collars on the shaft 142 are indicated at 174, 176. The annular collars on the shaft 144 are indicated at 178, 180. Similarly, the annular collars on the shaft 146 are indicated at 182, 184.

Typically, for an end effector having two working members, such as the clip applier 58, four spools are provided in the housing 53. The cable C1 is wrapped around one such spool, the cable C2 around another, the cables C3 and C4 around another, and the fourth spool being operatively connected to the shaft 14.1 to cause the angular displacement of the shaft in the direction of arrow H in FIG. 3, in response to angular displacement of that spool. It will be appreciated that the cables C3 and C4 can form opposed end portions of a single cable, a generally centrally disposed portion of which is wrapped around its associated spool.

It will be appreciated that when the shaft 14.1 is caused to displace angularly relative to the housing 53, the wrist mechanism 52 displaces angularly relative to the housing in sympathy with the shaft 14.1. Thus, the cables C1, C2, C3 and C4 are caused to twist along their lengths during such angular displacement of the shaft 14.1. It has been found that cables made of Tungsten provide sufficient strength, durability and bending properties where the cables C1, C2, C3 and C4 are wrapped around the spools and where they extend over the pulley sets 64, 66, 68 and 70.

Figure 3A:
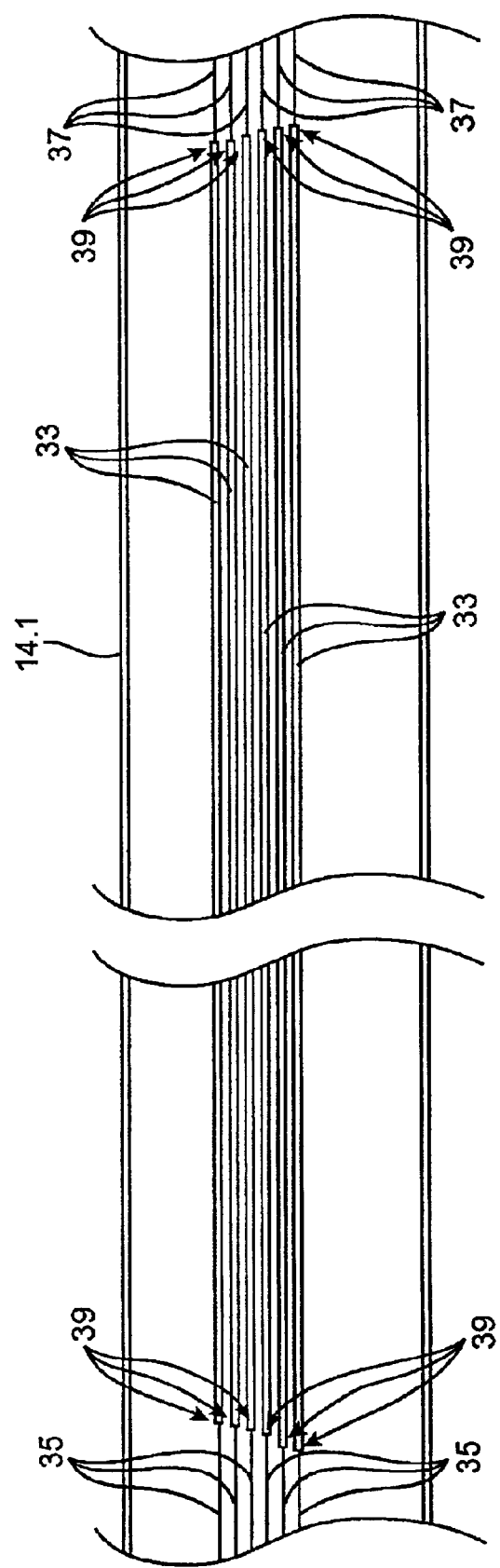
FIG. 3A shows a schematic sectional side view, at an enlarged scale, of part of an elongate shaft of the instrument shown in FIG. 3, and which further shows part of an elongate element actuation system of the instrument shown in FIG. 3.

To inhibit stretching of the cables along their lengths and along the shaft 14.1, elongate relatively rigid members, e.g., hypotube portions, are used. The hypotube portions are indicated in FIG. 3A by reference numeral 33. The opposed Tungsten cable portions are indicated at 35, 37, respectively.

Ends of the Tungsten cable portions are typically crimped in the ends of the hypotubes as indicated at 39. The hypotubes are typically hollow tubes having a cross-sectionally circular profile.

As mentioned earlier, the end effector 58 is in the form of a clip applier. In use, a clip 75, as indicated in FIG. 9, is positioned between the finger portions 58.3. Opposed limbs 75.1, 75.2 of the clip 75 are positioned in longitudinally extending recesses or seats 58.13 in each of the finger portions 58.1, 58.2.

Normally, in use, the end effector 58 is removed from the surgical site, a clip 75 is then positioned between the finger portions 58.3 and then the end effector 58 is reintroduced into the patient's body so as to apply or anchor the clip 75 where required. To apply the clip, the master controls are manipulated to cause the clip applier to close so as to bend the clip 75. When the clip 75 has been applied, the end effector 58 can again be removed from the surgical site, another clip 75 can then be positioned between the finger portions 58.3 and the end effector can again be introduced to the surgical site to apply that clip and so on, until all the required clips have been applied or anchored in position.

It will be appreciated that it is important that the clip is securely seated in the clip applier 58 until the clip applier is caused to anchor the clip in position. If the clip 75 is not securely seated, it could happen that the clip 75 becomes dislocated from the clip applier 58. In such a case, valuable time could be lost in trying to find and recover the clip 75 from the surgical site.

To cause the clip 75 to seat securely on the clip applier 58, the portions 58.1 58.2 are biased or urged in a closing direction so as to clamp the clip 75 in the opposed seats or recesses 58.13.

The biasing or urging arrangement to cause such clamping of the clip 75 in the seats 58.13, is generally indicated by reference numeral 58.14 in FIGS. 9, 12, 13 and 14.

The biasing arrangement 58.14 includes a generally arcuate slot 58.15 in each face 58.11 of the respective parts 58.1, 58.2. A leaf spring member 58.18 is located at an end region of each slot. A base portion 58.16 of the leaf spring is anchored in its associated slot. The leaf spring member 58.18 is generally cylindrical in shape and is typically made of a nickel titanium alloy available under the trade name Nitinol™. The leaf spring 58.18 protrudes from the slot in which it is anchored such that a free end is positioned in the slot of the opposing one of the parts 58.1, 58.2. The spring member 58.18 extends perpendicularly relative to a plane of movement of the parts 58.1, 58.2 in which plane of movement the finger portions 58.3 move toward and away from each other.

Thus, when the finger portions 58.3 are angularly displaced apart beyond a specific angle, e.g., 10°, the leaf spring members 58.15 abut. Angular displacement of the elongate portions beyond 10° causes the leaf spring members 58.15 to bend resiliently thus urging the elongate portions 58.3 to close so as to clamp the clip 75 in the slots 58.13. Alternatively, instead of a mechanical biasing means, such as the leaf or some other spring, software may be used to control the degree to which the finger portions may open. Upon opening the finger portions beyond the specified, predetermined angle, e.g., the software controls the finger portions to close back to the specified position, and in this way creates a virtual biasing mechanism. For this software embodiment to work, however, the clip applier tool should remain connected to the software in the control system so that the virtual biasing mechanism can serve its designated function.

Although the above disclosure concerns a biasing mechanism for holding the clip in place, a clip applier within the scope of the present invention may be constructed without such a mechanism, to hold a loaded clip by means of friction alone. In such case, each finger member of the clip applier would have an associated mechanical stop. This pair of mechanical stops would physically prevent the two finger portions from opening beyond a certain angle. To use friction to maintain a clip in position between the finger members upon loading, the finger members preferably would have a maximum open angle slightly less—by fractions of a degree—than the angle of the clip to be loaded. The finger members are opened with a low-torque software command that instructs the fingers to occupy a position past the mechanical stops, thereby guaranteeing that each member will come to rest at its mechanical stop and be urged against the stop. A low-torque command, preferably in the order of only several hundredths of a N-m, is preferred for this step to ensure correct positioning of the finger members without damaging the mechanism used to position the members against the stops. Upon loading, the inherent biasing force in the clip itself can help to hold the clip in place. For this mechanical stop embodiment, slots 58.13 may have an open distal portion to form a channel, so that the clip can slide between the finger members without becoming so compressed that it can no longer bias against the finger members and cannot be loaded. Once loaded, the clip applier can be closed with a much higher torque command—perhaps 5 to 10 times as much as the torque used to open the finger members—to provide the force necessary to apply the clip around the tissue of interest.

Figure 15:
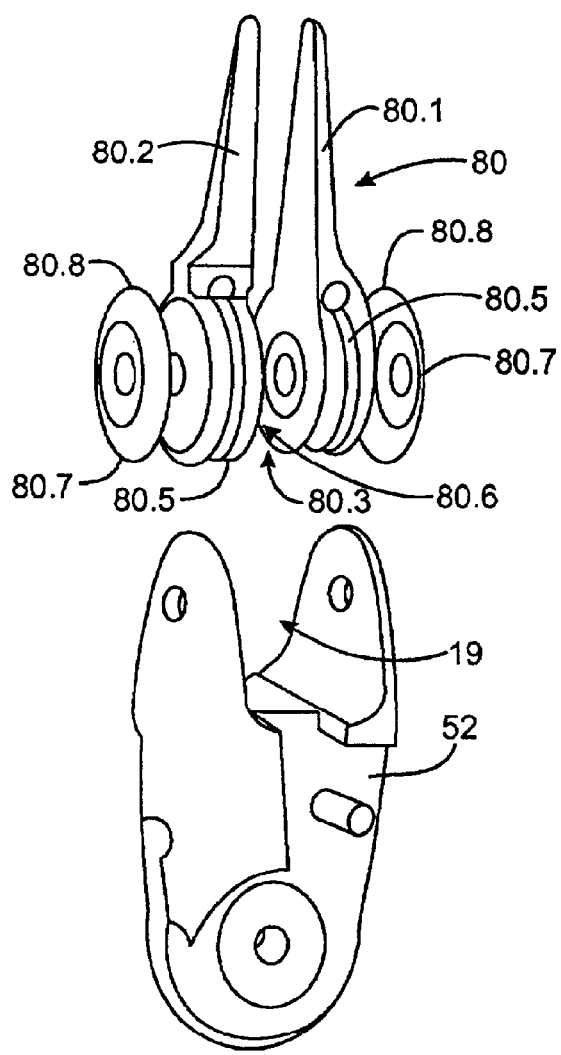
FIG. 15 shows an exploded three-dimensional view of surgical scissors in accordance with a preferred embodiment of the invention.
Figure 16:
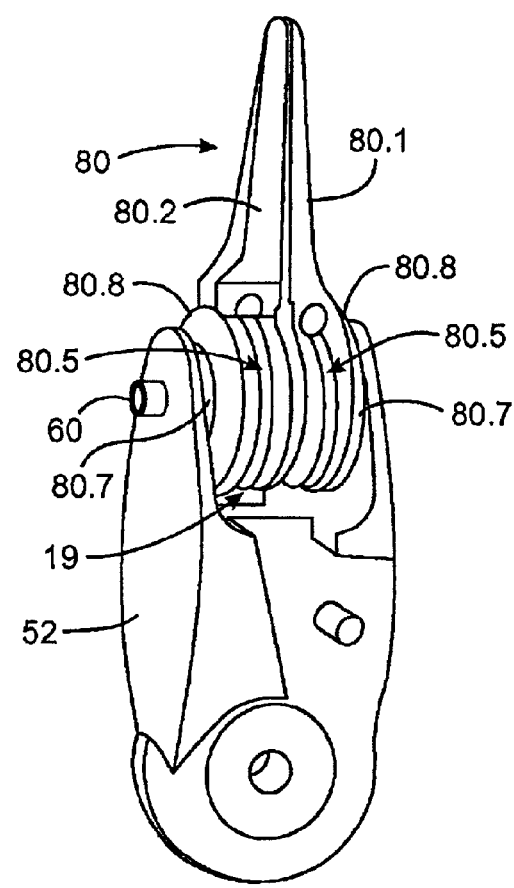
FIG. 16 shows an assembled three-dimensional view corresponding to FIG. 15.

Referring now to FIGS. 15 and 16, in which like reference numerals are used to designate similar parts unless otherwise stated, an end effector in the form of a scissors, generally indicated by reference numeral 80, will now be described.

The scissors 80 is mounted on a wrist member arrangement similar to that described above with reference to FIGS. 5, 6 and 7. The scissors 80 has opposed members or blades 80.1, 80.2. Opposed slots 80.3 are provided in pulley portions 80.5. Opposed pins 80.6 are also provided. The pin 80.6 of the one member 80.1, 80.2 rides in the slot 80.3 of the other of the members 80.1, 80.2. The pin and slot arrangement inhibits the blades 80.1, 80.2 of the scissors from opening beyond a predetermined angle, e.g., 20°, or closing beyond a certain point (e.g. 0 or even −5 degrees).

During a cutting action, it is important that the blades 80.1, 80.2 of the scissors ride against each other. To urge the blades together, a biasing means such as spring washers, e.g., bellville washers, 80.7 sandwich the members 80.1, 80.2 in the clevis 19. The spring washers 80.7 have inwardly disposed circumferential edges 80.8 arranged to urge the blades of the scissors together at a position beyond the pivotal connection 60.

Referring now to FIGS. 17, 18 and 19, in which like reference numerals are used to designate similar parts unless otherwise stated, an end effector in the form of a cautery blade 90 is indicated. The blade 90 is removably mountable on a pulley arrangement 92.

The pulley arrangement 92 forms part of a wrist mechanism generally indicated by reference numeral 94. The wrist mechanism 94 is similar to the wrist mechanism 50 save that it has single pulleys 96, 98, 100, 102 as opposed to the pulley sets 64, 66, 68 and 70. It will be appreciated that the blade 90 forms an end effector having a single operative member as opposed to the clip applier 58 and scissors 80 described above which have two operative members each. Thus, operation of the blade involves a single pulley arrangement 92 as opposed to a double pulley arrangement as is the case with the clip applier 58 and scissors 80. Thus, only the single pulleys 96, 98, 100 and 102 are required, and only one of the cables C1, C2. Accordingly, in such a case, only three spools are provided in the housing 53 as opposed to the four spools described earlier.

The blade 90 has a generally hook-shaped portion 90.1. The hook-shaped portion 90.1 is removably insertable into a slot or hole 92.1 defined in the pulley arrangement 92. It will be appreciated that when the hook-shaped portion 90.1 of the blade 90 is inserted into the slot, a free end 90.2 of the hook-shaped portion 90.1 is marginally and resiliently bent in the direction of arrow Z as shown in FIG. 19. Once inserted, and when the blade 90 is urged to be removed from the slot 92.1, frictional engagement of the end 90.2 against an inner wall of the slot 92.1 tends to urge the free end 90.2 in an outward direction as indicated by arrow X, thus locking the hook-shaped portion 90.1 in the slot 92.1. Locking the blade in a mounted condition on the pulley arrangement 92 is important so as to inhibit the blade from becoming dismounted from the pulley arrangement 92 during a surgical procedure. However, when removed from the surgical site, the blade 90 can be removed when a sufficient pulling force is applied so as to overcome the frictional locking action in the slot 92.1.

It will be appreciated that a variety of different end effectors comprising only one operative member, e.g., a scalpel, dissection finger, etc., can be removably mounted on the pulley arrangement 92 in this manner. The blade 90 is simply used as an example of one such end effector. It will further be appreciated that a similar releasably mountable arrangement can be employed on a double pulley arrangement to enable interchangeability of end effectors having two working members, e.g., clip appliers, scissors, pliers, forceps, two-fingered blunt dissection tools, or the like.

Figure 20:
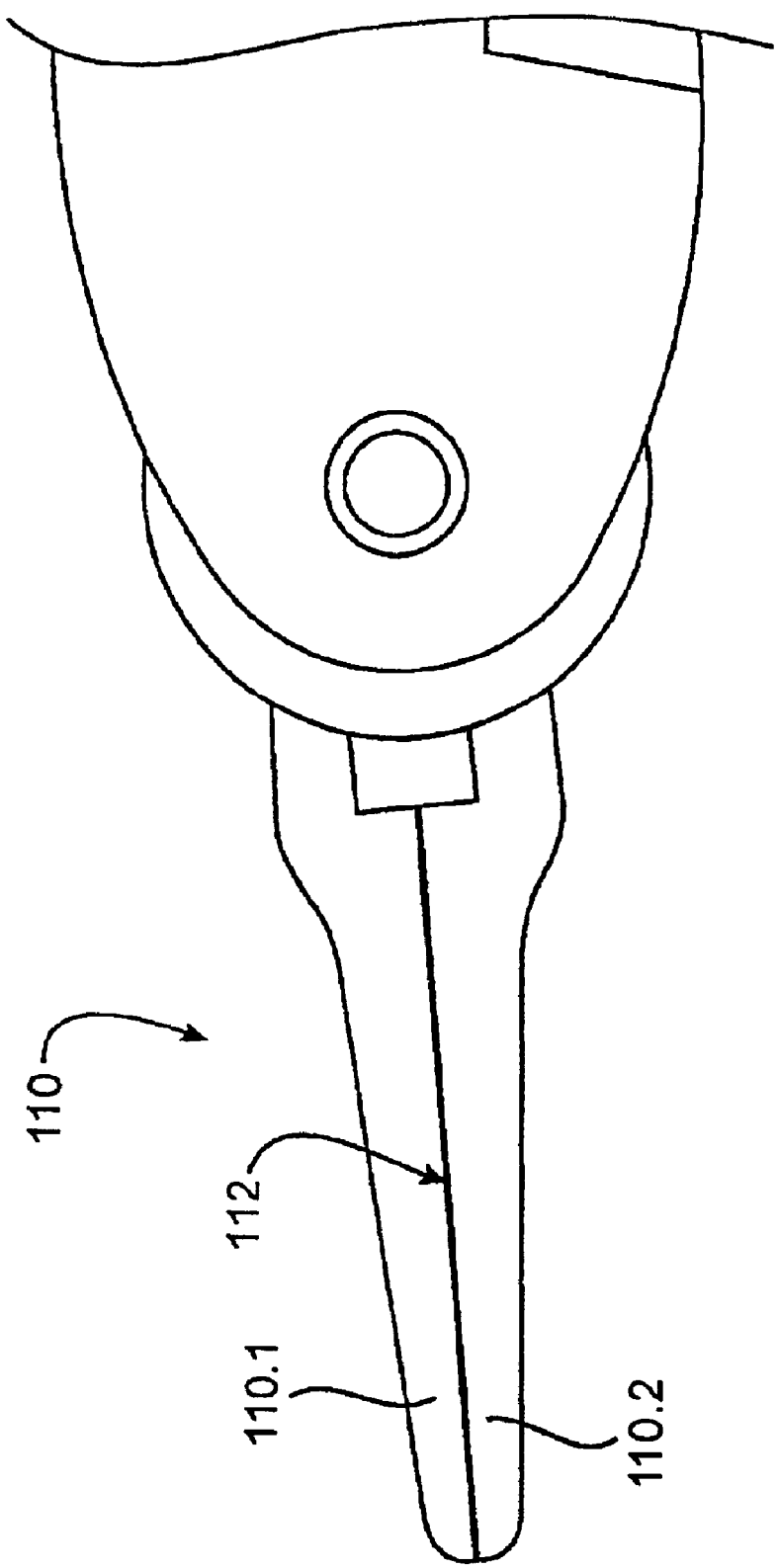
FIG. 20 shows a side view of micro forceps in accordance with a preferred embodiment of the invention.

Referring now to FIG. 20 of the drawings, an end effector in the form of forceps is generally indicated by reference numeral 110. The forceps 110 is mounted on a wrist mechanism similar to the wrist mechanism 50.

The forceps 110 has two working members 110.1, 110.2. The working members 110.1, 110.2 are slightly bent to define a space 112 between them. In use, it is difficult to provide force feedback to the master controls. Thus, it could happen that an organ, or tissue, or the like, can be grasped by forceps with too much force that may unnecessarily damage such organ or tissue.

To inhibit this, the space 112 is provided. The members 110.1, 110.2 have a degree of resilience. Thus, when the forceps is used, the surgeon manipulating the master controls can obtain an indication of the force applied when grasping with the forceps 110 by visually monitoring resilient deflection of the members 110.1, 110.2 relative to each other.

Figure 21:
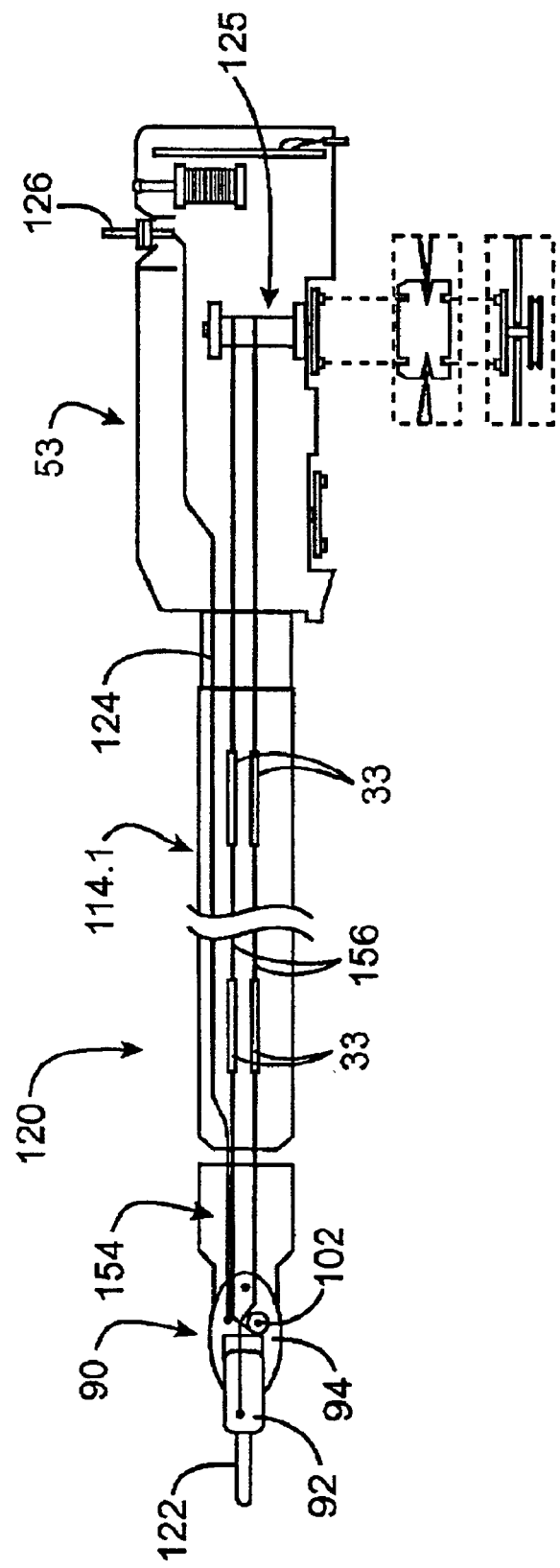
FIG. 21 shows a schematic side view of a cautery surgical instrument in accordance with a preferred embodiment of the invention.

Referring now to FIG. 21 of the drawings, in which like reference numerals as used specifically in FIGS. 17, 18 and 19 to designate similar parts unless otherwise indicated, an electrocautery surgical instrument is generally indicated by reference numeral 120. This electrocautery instrument may comprise an instrument that applies high-frequency alternating current to surrounding tissue, thereby to cause the tissue temperature to rise to the point where the tissue is cut or coagulates, or may comprise an instrument that applies heat to tissue by means of electrically generated heat inside the instrument. The nature of the cauterizing action should not be understood as limiting to this invention.

The instrument 120 is in a form generally similar to that shown in FIG. 3 and has a wrist mechanism 90 similar to that indicated in FIGS. 16, 17 and 18. Thus, an electrode 122 of the instrument 120 can be releasably mountable on its associated pulley arrangement 92 to enable interchanging with other end effectors, e.g., a scalpel, cautery blade, or the like.

It will be appreciated that the electrocautery instrument 120 is used to generate an electrical current at a surgical site so as to burn or seal, e.g., ruptured blood vessels. In use, the patient is earthed and a voltage is supplied to the electrode 122. An electrically conductive cable 124 extends from a plug 126 on the housing 53 to the electrode 122. This conductive cable, or cautery wire, preferably includes a "service loop" (not shown) around the distal joint axis 60. This service loop single, loose wrap around the joint permits rotation of the cautery blade about the axis without placing undue stress or stretch on the wire during such rotation. It will be appreciated that, in use, the plug 126 is releasably connected to an appropriate electrical source. The plug 126 is typically a conventional banana-type plug. The housing 53 is typically of a non-conductive plastics material. It has been found that it is necessary to insulate the electrode 122 from the rest of the instrument 120 so as to inhibit current leakage from the electrode 122 to the rest of the instrument 120. It will be appreciated that should the distance between the electrode 122 and the patient be relatively great when a voltage is applied, current may jump from the electrode 122 to other conductive parts of the instrument. In such a case, current can be passed from the instrument 120 to the patient along a path of least resistance, e.g., at the entry port coincident with the center of rotation 49. This may cause unnecessary burning at the entry port. Furthermore, the current may be passed along the instrument 120 to the telesurgical system in general and may be damaging to sensitive electronics, e.g., forming part of the endoscope and viewer arrangement.

Accordingly, the wrist mechanism 90 where necessary is made of non-conductive material. The wrist member 92 and the various pulleys are typically made from non-conductive plastic, e.g., polyetherimide or ULTEM™. Alternatively, a conductive wrist can be sheathed in a nonconductive material. The conductive cable 124 is typically sheathed in an insulative material such as, e.g., polytetrafluoroethylene or TEFLON™. The cable 124 typically exits the shaft 14.1 through a hole, similar to one of the holes 47, in the base of a clevis similar to the clevis 17 in FIGS. 17, 18 and 19. From such a hole, the cable is threaded through spaces resulting from the fact that single pulleys 96, 98, 100 and 102 are present in the wrist mechanism 90 as opposed to pulley sets 64, 66, 68 and 70 shown in FIGS. 5, 6 and 7. Such spaces are indicated by reference numeral 150 in FIG. 17. As can best be seen in FIG. 19, the conductive cable terminates at a conductive connection within the pulley arrangement 92. The electrode 122 is removably mountable on the pulley arrangement 92. Accordingly, a suitable conductive seat or sleeve is provided in the pulley arrangement 92 to provide an electrical connection to the electrode 122 when in a mounted condition. The conductive cable is conductively connected to such a conductive seat or sleeve.

The shaft 114.1 is typically made entirely from a non-conductive material, or at least sheathed in such a material, to insulate the shaft from the patient, in particular in the region of the port of entry coincident with the center of rotation 49. The preferred nonconductive material for the shaft 114.1 comprises an electrical grade fiberglass/vinyl ester composite material. A shaft of stainless steel or carbon fiber may be coated with, e.g., a nylon or parylene, such as Nylon-11 or Parylene C. The cables that extend internally along the shaft 114.1 typically have non-conductive portions 156. Such nonconductive or insulative portions are typically high strength polymer cables in the form of, e.g., a liquid crystal polymer (LCP) such as VECTRAN™, a liquid crystal polyester. The VECTRAN™ portions are typically crimped to opposed hypotube lengths. Opposed ends of such hypotubes are in turn typically crimped to tungsten cable lengths which extend to the spools in the housing 53 and to the wrist mechanism 92, respectively.

It will be appreciated that the pulley arrangement 92, the wrist member 94 and a member 154 defining the clevis 17 and which is mounted on the end 14.3 of the shaft 14.1 are typically of an insulative material such as, e.g., ULTEM™.

It is envisaged that a surgical instrument 120 be used as a universal instrument which can be used in conjunction with any end effector, whether or not the end effector is to be used for electrocautery purposes. Where an end effector, e.g., a scalpel, is to be used, the electrode 122 is replaced by an end effector in the form of a scalpel. The scalpel is naturally not an electrocautery end effector so that when it is used, the electrically insulative elements of the tool 120 are redundant. By using the tool 120 as a universal tool in this manner, the number of instruments and the cost to a user is reduced.

What is claimed is:

1. A minimally invasive surgical instrument comprising:
   a pair of end effector mounting formations, each formation arranged to carry an end effector element and to be displaceable so that the end effector elements move toward and away from each other in a plane of movement; and
   an urging arrangement arranged to urge the end effector elements toward each other when they are moved apart beyond a predetermined amount, the urging arrangement comprising a resilient urging member arranged to cooperate with the mounting formations so as to be resiliently deformed upon movement of the end effector elements beyond the predetermined amount, thereby to urge the end effector elements toward each other; wherein each and effector element comprises a finger portion of a clip applier.

2. The instrument of claim 1, wherein the resilient urging member extends at an angle relative to the plane of movement.

3. The instrument of claim 1, wherein the clip applier is adapted to releasably hold a clip between two finger portions of the clip applier.

4. The instrument of claim 1, wherein at least one of the finger portions is integrally formed with its corresponding end effector mounting formation.

5. The instrument of claim 1, wherein each end effector mounting formation comprises a pulley portion.

6. The instrument of claim 5, wherein each pulley portion comprises a circumferentially extending channel adapted to receive an elongate element.

7. The instrument of claim 5, wherein each pulley portion comprises an axially-extending, centrally disposed hole adapted to receive a pivotal pin of a pivotal connection.

8. The instrument of claim 1, wherein the urging arrangement comprises a spring member.

9. The instrument of claim 8, wherein the spring member is a leaf spring member.

10. The instrument of claim 9, wherein the leaf spring member comprises an alloy comprising nickel end titanium.

11. The instrument of claim 1, wherein the predetermined amount corresponds to an angle between the end effector elements of about 10 degrees.

12. The instrument of claim 1, wherein the urging arrangement is controlled by a software module.

13. The instrument of claim 1, further comprising a mechanical stop that prevents the end effector elements from opening beyond a certain amount.

14. The instrument of claim 1, wherein the pair of end effector mounting formations are coupled about a common pivotal connection.

15. The instrument of claim 14, wherein the common pivotal connection is coupled with a wrist member.

16. The instrument of claim 15, wherein the wrist member is coupled with a working end of an elongate shaft.

17. The instrument of claim 16, further comprising at least one remote actuator operatively connected to the wrist member that can cause the wrist member to pivot in response to actuation of the actuator.

18. The instrument of claim 17, further comprising a housing disposed on elongate shaft opposite the working end, wherein the housing is adapted to releasably couple the instrument with a robotic arm of a minimally invasive telesurgical system.

19. A minimally invasive surgical instrument for use with a robotic surgical system, the robotic surgical system providing master-slave telesurgery in response to input from a surgeon, the surgical instrument comprising;
- a pair of end effector mounting formations, each formation arranged to carry an end effector element and to be displaceable so that the end effector elements move toward and away from each other in a plane of movement; and
- an urging arrangement arranged to urge the end effector elements toward each other when they are moved apart beyond a predetermined amount, the urging arrangement comprising at least one elongate resilient urging member having a first end anchored on a first of the mounting formations and an opposed end intruding into a space defined by the second of the mounting formations, the opposed end abutting part of the second mounting formation when the end effector elements are moved apart by the predetermined amount, such that the resilient member is resiliently deformed by that part of the second mounting formation in response to the end effector elements being urged apart beyond the predetermined amount, thereby to urge the end effector elements toward each other.

20. The instrument of claim 19, wherein each end effector element comprises a finger portion of a clip applier.

21. The instrument of claim 20, wherein the clip applier is adapted to releasably hold a clip between two finger portions of the clip applier.

22. The instrument of claim 20, wherein at least one of the finger portions is integrally formed with its corresponding end effector mounting formation.

23. The instrument of claim 20, wherein each end effector mounting formation comprises a pulley portion.

24. The instrument of claim 23, wherein each pulley portion comprises a circumferentially extending channel adapted to receive elongate element.

25. The instrument of claim 23, wherein each pulley portion comprises an axially-extending, centrally disposed hole adapted to receive a pivotal pin of a pivotal connection.

26. The instrument of claim 19, wherein the urging arrangement comprises a spring member.

27. The instrument of claim 26, wherein the spring member is a leaf spring member.

28. The instrument of claim 27, wherein the leaf spring member comprises an alloy comprising nickel and titanium.

29. The instrument of claim 19, wherein the predetermined amount corresponds to an angle between the end effector elements of about 10 degrees.

30. The instrument of claim 19, wherein the urging arrangement is controlled by a software module.

31. The instrument of claim 19, further comprising a mechanical stop that prevents the end effector elements from opening beyond a certain amount.

32. The instrument of claim 19, wherein the pair of end effector mounting formations are coupled about a common pivotal connection.

33. The instrument of claim 32, wherein the common pivotal connection is coupled with a wrist member.

34. The instrument of claim 33, wherein the wrist member is coupled with a working end of an elongate shaft.

35. The instrument of claim 34, further comprising at least one remote actuator operatively connected to the wrist member that can cause the wrist member to pivot in response to actuation of the actuator.

36. The instrument of claim 35, further comprising a housing disposed on the elongate shaft opposite the working end, wherein the housing is adapted to releasably couple the instrument with a robotic arm of a minimally invasive telesurgical system.

37. A minimally invasive surgical instrument for use with a robotic surgical system, the robotic surgical system providing master-slave telesurgery in response to input from a surgeon, the surgical instrument comprising;
- a pair of end effector mounting formations, each formation arranged to carry an end effector element and to be displaceable so that the end effector elements move toward and away from each other in a plane of movement;
- an urging arrangement arranged to urge the end effector elements toward each other when they are moved apart beyond a predetermined amount, the urging arrangement comprising at least one resilient member;
- wherein the urging arrangement comprises a spring member.

38. The instrument of claim 37, wherein the at least one resilient member comprises an alloy comprising nickel and titanium.

39. The instrument of claim 37, wherein each end effector element comprises a finger portion of a clip applier.

40. The instrument of claim 39, wherein the clip applier is adapted to releasably hold a clip between two finger portion of the clip applier.

41. The instrument of claim 39, wherein at least one of the finger portions is integrally formed with its corresponding end effector mounting formation.

42. The instrument of claim 39, wherein each end effector mounting formation comprises a pulley portion.

43. The instrument of claim 42, wherein each pulley portion comprises a circumferentially extending channel adapted to receive an elongate element.

44. The instrument of claim 42, wherein each pulley portion comprises an axially-extending, centrally disposed hole adapted to receive a pivotal pin of a pivotal connection.

45. The instrument of claim 37, wherein the spring member is a leaf spring member.

46. The instrument of claim 45, wherein the leaf spring member comprises an alloy comprising nickel and titanium.

47. The instrument of claim 37, wherein the predetermined amount corresponds to an angle between the end effector elements of about 10 degrees.

48. The instrument of claim 37, wherein the urging arrangement is controlled by a software module.

49. The instrument of claim 37, further comprising a mechanical stop that prevents the end effector elements from opening beyond a certain amount.

50. A minimally invasive surgical instrument for use with a robotic surgical system, the robotic surgical system providing master-slave telesurgery in response to input from a surgeon, the surgical instrument comprising;
- a pair of end effector mounting formations, each formation arranged to carry an end effector element and to be displaceable so that the end effector elements move toward and away from each other in plane of movement;
- an urging arrangement arranged to urge the end effector elements toward each other when they are moved apart beyond a predetermined amount, the urging arrangement comprising at least one resilient member;
- wherein the pair of end effector mounting formations are coupled about a common pivotal connection.

51. The instrument of claim 50, wherein the common pivotal connection is coupled with a wrist member.

52. The instrument of claim 51, wherein the wrist member is coupled with a working end of an elongate shaft.

53. The instrument of claim 52, further comprising at least one remote actuator operatively connected to the wrist member that can cause the wrist member to pivot in response to actuation of the actuator.

54. The instrument of claim 53, further comprising a housing disposed on the elongate shaft opposite the working end, wherein housing is adapted to releasably couple the instrument with a robotic arm of a minimally invasive telesurgical system.

* * * * *